US012797179B2

(12) United States Patent
Nakayama et al.

(10) Patent No.: US 12,797,179 B2
(45) Date of Patent: Nov. 17, 2026

(54) CONNECTIVE-TISSUE BODY AND METHOD FOR PRODUCING SAME

(71) Applicant: BIOTUBE CO., LTD., Tokyo (JP)

(72) Inventors: Yasuhide Nakayama, Tokyo (JP); Yasushi Sato, Tokyo (JP); Takeshi Terazawa, Tokyo (JP)

(73) Assignee: BIOTUBE CO., LTD., Tokyo (JP)

( * ) Notice: Subject to any disclaimer, the term of this patent is extended or adjusted under 35 U.S.C. 154(b) by 1146 days.

(21) Appl. No.: 17/624,819

(22) PCT Filed: Jul. 10, 2020

(86) PCT No.: PCT/JP2020/027019
§ 371 (c)(1),
(2) Date: Jan. 4, 2022

(87) PCT Pub. No.: WO2021/006335
PCT Pub. Date: Jan. 14, 2021

(65) Prior Publication Data
US 2022/0257362 A1 Aug. 18, 2022

(30) Foreign Application Priority Data
Jul. 10, 2019 (JP) ................................ 2019-128790

(51) Int. Cl.
*A61F 2/07* (2013.01)
*A61F 2/06* (2013.01)
(Continued)

(52) U.S. Cl.
CPC ................ *A61F 2/062* (2013.01); *A61F 2/07* (2013.01); *A61F 2/2415* (2013.01); *A61L 27/24* (2013.01);
(Continued)

(58) Field of Classification Search
CPC .......... A61F 2/062; A61F 2/07; A61F 2/2415; A61F 2/24; A61F 2/02; A61F 2/08;
(Continued)

(56) References Cited

U.S. PATENT DOCUMENTS 3,110,212 A * 11/1963 Wing .................... F16B 37/122
411/80.6
6,537,567 B1 * 3/2003 Niklason ................ C12M 21/08
435/395
(Continued)

FOREIGN PATENT DOCUMENTS

CN 206621452 U 11/2017
JP 2003534102 11/2003
(Continued)

OTHER PUBLICATIONS

Nakayama et al., "Water-soluble argatroban for antithrombogenic surface coating of tissue-engineered cardiovascular tissues" Society for Biomaterials. 2011.
(Continued)

*Primary Examiner* — Christine H Matthews
*Assistant Examiner* — Brooke Nicole Kohutka
(74) *Attorney, Agent, or Firm* — Maschoff Brennan

(57) ABSTRACT

A method to produce a connective tissue body including biological origin tissue including collagen includes placing, in a living body, a connective tissue body formation substrate including a tissue formation surface that is at least partially made of a polymer material. The method includes removing air percutaneously and transluminally to an outside of the living body from a space in the living body in which the connective tissue body formation substrate is placed. The method includes allowing a connective tissue body to form on the tissue formation surface. The method includes removing, from the living body, the connective
(Continued)

tissue body formation substrate on which the connective tissue body is formed. The method includes peeling off the connective tissue body from the connective tissue body formation substrate.

9 Claims, 16 Drawing Sheets

(51) Int. Cl.

| | |
|---|---|
| ***A61F 2/24*** | (2006.01) |
| ***A61L 27/24*** | (2006.01) |
| ***A61L 27/36*** | (2006.01) |
| ***A61L 27/56*** | (2006.01) |
| ***A61M 27/00*** | (2006.01) |
| *A61F 2/04* | (2013.01) |

(52) U.S. Cl.
CPC ............... *A61L 27/36* (2013.01); *A61L 27/56* (2013.01); *A61F 2002/044* (2013.01); *A61F 2002/047* (2013.01); *A61F 2002/048* (2013.01); *A61F 2002/072* (2013.01); *A61F 2240/001* (2013.01); *A61M 27/00* (2013.01)

(58) Field of Classification Search
CPC ........ A61F 2/04; A61F 2/06; A61F 2002/044; A61F 2002/047; A61F 2002/048; A61F 2002/072; A61F 2002/046; A61F 2240/001; A61F 2210/0076; A61F 2250/0015; A61L 27/36; A61L 27/56; A61L 27/3662; A61L 27/3679; A61L 27/50; A61L 27/507; A61L 2430/10; A61L 2430/20; A61L 2430/22
See application file for complete search history.

(56) References Cited

U.S. PATENT DOCUMENTS

| | | | | |
|---|---|---|---|---|
| 9,408,956 | B2 * | 8/2016 | Zamierowski | A61M 1/916 |
| 10,842,645 | B2 * | 11/2020 | Nebosky | A61F 2/447 |
| 2002/0120348 | A1 * | 8/2002 | Melican | A61F 2/0045 623/23.72 |
| 2003/0133967 | A1 * | 7/2003 | Ruszczak | A61L 27/44 424/443 |
| 2004/0002055 | A1 | 1/2004 | Andre et al. | |
| 2005/0208478 | A1 | 9/2005 | Andre et al. | |
| 2007/0154515 | A1 * | 7/2007 | Johnson | A61L 27/3645 424/423 |
| 2009/0269387 | A1 | 10/2009 | Zubery et al. | |
| 2010/0249719 | A1 * | 9/2010 | Fojtik | A61M 25/104 604/218 |
| 2011/0281351 | A1 | 11/2011 | Adachi et al. | |
| 2012/0195863 | A1 * | 8/2012 | Alt | A01N 1/142 435/325 |
| 2013/0121970 | A1 * | 5/2013 | Owens | A61K 47/46 623/23.72 |
| 2017/0319745 | A1 | 11/2017 | Nakayama et al. | |
| 2018/0008391 | A1 * | 1/2018 | Li | A61L 27/48 |
| 2019/0083225 | A1 | 3/2019 | Nakayama et al. | |

FOREIGN PATENT DOCUMENTS

| | | | | |
|---|---|---|---|---|
| JP | 6033979 | B1 | 11/2016 | |
| KR | 20150103470 | A | 9/2015 | |
| WO | WO-2013176131 | A1 * | 11/2013 | C12M 25/14 |
| WO | 2016076416 | A1 | 5/2016 | |
| WO | WO-2021110908 | A1 * | 6/2021 | A61L 27/54 |

OTHER PUBLICATIONS

Nam, K. "Development of artificial collagen matrix using fibrillized collagen matrix" Rep. Grant. Res., Asahi Glass Foundation (2011).
Extended European Search Report dated Jun. 13, 2023 as received in Application No. 20836404.2.
Second Office Action dated Aug. 16, 2025, issued in Chinese Patent Application No. 202080045562.1.

* cited by examiner

CONNECTIVE-TISSUE BODY AND METHOD FOR PRODUCING SAME

TECHNICAL FIELD

The present invention relates to a connective tissue body including biological origin tissue and a method for producing the same.

BACKGROUND ART

When a foreign substance penetrates the skin of a living body, the self-defensive mechanism of the living body causes subcutaneous fibroblasts to accumulate around the foreign substance, producing collagen enclosing the foreign substance. This phenomenon is commonly referred to as an encapsulation reaction. In recent years, regenerative medicine for artificially regrowing lost tissues and organs has been actively studied, and the use of encapsulation reactions for regenerative medicine has been proposed.

For example, Patent Document 1 (International Publication No. WO2016/076416) discloses a connective tissue body formation substrate having two opposed tissue formation surfaces. This substrate is placed in a living body so that a connective tissue body is formed in the tissue formation space between the two surfaces by collagen produced by an encapsulation reaction.

Specifically, the disclosed connective tissue body formation substrate includes a cylindrical substrate and a core member inserted in the cylindrical substrate. A tubular connective tissue body is formed in the tissue formation space between the substrate and the core member. The tubular connective tissue body is intended to be used as an artificial blood vessel or the like. Patent Document 1 also describes that a connective tissue formation substrate having two opposed planar substrates may be used to form a film connective tissue body. It also describes the formation of an artificial valve having multiple valve leaflets to be used as a heart valve, for example.

Patent Document 1: International Publication No. WO2016/076416

Non-Patent Document

Non-patent Document 1: Journal of Biomedical Materials Research Part B 2011:99B:420-430.

SUMMARY

However, the connective tissue body formed by the method disclosed in Patent Document 1 has insufficient surface strength. For example, Non-Patent Document 1 (Journal of Biomedical Materials Research Part B 2011: 99B:420-430) describes that blood may permeate into the connective tissue body when used for a structure in a living body, such as an artificial blood vessel or an artificial valve, increasing the possibility of thrombus formation. Surface treatment such as antithrombogenic material coating is therefore needed.

In addition, when the formed connective tissue body is used for a structure in a living body, such as an artificial esophagus, an artificial lymphatic vessel, an artificial diaphragm, an artificial urinary duct, or an artificial urethra, that comes into contact with fluid components in the body, such as body fluid, digestive juice, and excretions, moisture may permeate into the tissue, swelling and thus weakening the tissue. Furthermore, the thick connective tissue body has insufficient overall strength and thus cannot serve as tissue of locomotor apparatus such as an artificial tendon or an artificial ligament. For example, when an artificial structure such as a stent is enclosed in the tissue body, the artificial structure may be displaced in the tissue, causing the tissue shape to be unstable.

In view of the above problems, it is an objective of the present invention to increase the strength of a surface of a connective tissue body that is obtained through an encapsulation reaction and to be used for a structure in a living body such as an artificial blood vessel, an artificial valve, an artificial esophagus, an artificial lymphatic vessel, an artificial diaphragm, an artificial urinary duct, and an artificial urethra, or increase the strength of a whole connective tissue body that is used for a structure in a living body such as an artificial tendon and an artificial ligament, so as to prevent thrombus formation and swelling caused by blood or body fluid permeating the connective tissue body. Another objective is to stabilize an artificial structure enclosed in a tissue body so that the enclosed artificial structure is not displaced in the tissue body when used for an artificial trachea, a stent graft, or a covered stent, for example.

As a result of diligent studies, the present inventors have found that the above objectives can be achieved by forming a dense surface layer having dense tissue on the surface of the connective tissue body, and completed the following invention.

[1] A connective tissue body comprising biological origin tissue including collagen, wherein a surface layer forming a surface of the connective tissue body includes a dense surface layer in which tissue is denser than in a portion other than the surface layer.

[2] The connective tissue body according to [1], wherein the collagen includes fibrous collagen.

[3] The connective tissue body according to [2], wherein the fibrous collagen is flat and smooth at a surface of the dense surface layer.

[4] The connective tissue body according to [2] or [3], wherein the fibrous collagen in a portion other than a surface of the dense surface layer is arranged in a mesh pattern in an intersecting manner.

[5] The connective tissue body according to any one of [1] to [4], wherein a ratio of a tissue density of the surface layer to a tissue density of the portion other than the surface layer that is calculated along a thickness direction is greater than or equal to 1.1.

[6] The connective tissue body according to any one of [1] to [5], wherein a dissimilar member is embedded therein.

[7] The connective tissue body according to [6], wherein the dense surface layer is formed around the dissimilar member.

[8] The connective tissue body according to any one of [1] to [7], wherein the connective tissue body is formed by an encapsulation reaction.

[9] A method for producing a connective tissue body including biological origin tissue including collagen, the method comprising:

placing, in a living body, a connective tissue body formation substrate including a tissue formation surface that is at least partially made of a polymer material;

removing air percutaneously and transluminally to an outside of the living body from a space in the living body in which the connective tissue body formation substrate is placed;

allowing a connective tissue body to form on the tissue formation surface;

removing, from the living body, the connective tissue body formation substrate on which the connective tissue body is formed; and peeling off the connective tissue body from the connective tissue body formation substrate.

[10] A connective tissue body that is formed by placing, in an environment in a living body other than a human body, a tissue body formation substrate that includes a tissue formation surface for separating the environment where a biological tissue material is present from a space for forming the connective tissue body, the tissue body formation substrate including a hole for connecting the space and the environment to each other to allow for entry of connective tissue into the space, and removing air from a space in which the tissue body formation substrate is placed from an outside of the living body, wherein the tissue formation surface includes a polymer material or a metal material, the connective tissue body includes biological origin tissue including collagen and is used for tissue in a living body, a whole of a surface layer forming a surface of the connective tissue body that is in contact with the tissue formation surface is a dense surface layer in which tissue is denser than in a portion other than the surface layer, and for the dense surface layer, a ratio of a tissue density of the surface layer to a tissue density of the portion other than the surface layer that is calculated along a thickness direction is greater than or equal to 1.1.

[11] A method for producing a connective tissue body that includes biological origin tissue including collagen and is used for tissue in a living body, the method comprising:

placing, in a living body other than a human body, a connective tissue body formation substrate including a tissue formation surface that is at least partially made of a polymer material;

removing air percutaneously and transluminally to an outside of the living body from a space in the living body in which the connective tissue body formation substrate is placed;

allowing a connective tissue body to form on the tissue formation surface;

removing, from the living body, the connective tissue body formation substrate on which the connective tissue body is formed; and peeling off the connective tissue body from the connective tissue body formation substrate.

[12] The method for producing a connective tissue body according to [11], wherein the connective tissue body is formed by an encapsulation reaction.

[13] A connective tissue body for regenerative medicine, comprising:

a surface layer including first fibrous collagen of biological origin; and a non-surface-layer portion including second fibrous collagen of biological origin, wherein the first fibrous collagen in the surface layer has a first microscopic structure and a first density, the second fibrous collagen in the non-surface-layer portion has a second microscopic structure different from the first microscopic structure, and a second density less than the first density, and the surface layer and the non-surface-layer portion form a wall dissociation structure that results from a difference between the first density of the first fibrous collagen and the second density of the second fibrous collagen and a difference between the first microscopic structure of the first fibrous collagen and the second microscopic structure of the second fibrous collagen.

[14] The connective tissue body according to [13], wherein the surface layer and the non-surface-layer portion form a layer boundary that results only from the difference between the first density and the second density and the difference between the first microscopic structure and the second microscopic structure.

[15] The connective tissue body according to [13], wherein the first microscopic structure and the first density impart a first blood permeation resistance to the surface layer, the second microscopic structure and the second density impart a second blood permeation resistance to the non-surface-layer portion, and the first blood permeation resistance of the surface layer is higher than the second blood permeation resistance of the non-surface-layer portion.

According to the present invention, a connective tissue body is provided that has improved strength so as to prevent blood from permeating therein and forming thrombi when the connective tissue body is used for a structure in a living body, such as an artificial blood vessel or an artificial valve.

In addition, when a dissimilar member, such as an artificial structure, is enclosed in the connective tissue body, the dissimilar member is stabilized and not displaced in the connective tissue body.

MODES FOR CARRYING OUT THE INVENTION

[Connective Tissue Body]

Figure 1:
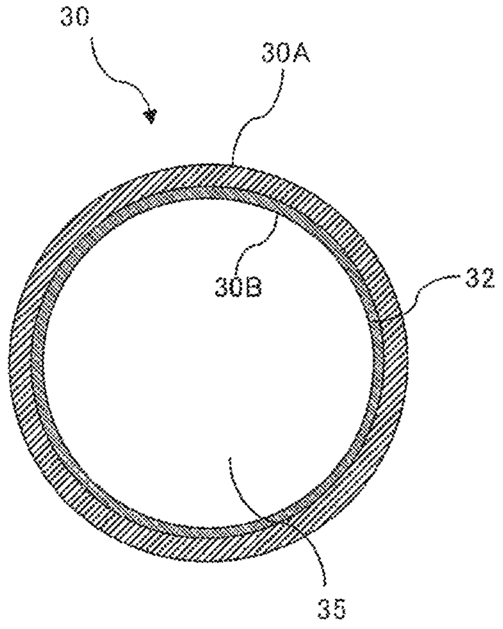
FIG. 1 is a schematic cross-sectional view showing an embodiment of a connective tissue body.

A connective tissue body according to the present invention includes collagen and biological origin tissue. The connective tissue body according to the present invention is typically formed by an encapsulation reaction. An encapsulation reaction is a reaction in which a biological tissue material, such as fibroblasts, accumulates around a foreign substance (a connective tissue body formation substrate described below) placed in an environment where the biological tissue material is present, such as under the skin of a living body, so that collagen is produced to encapsulate the foreign substance.

The connective tissue body contains collagen produced by the encapsulation reaction as the main component. The connective tissue body may also contain other biological tissue materials such as fibroblasts. A part or whole of the collagen of the connective tissue body forms fibrous collagen.

As used herein, the "biological tissue material" refers to a substance required to form a desired biological origin tissue and includes animal cells such as fibroblasts, smooth muscle cells, endothelial cells, stem cells, ES cells, and iPS cells, various proteins (collagen, elastin), saccharides such as hyaluronic acid, and other various physiologically active substances present in living bodies such as cell growth factors and cytokine. This "biological tissue material" includes those originated from mammals such as humans, dogs, cows, pigs, goats, and sheep, birds, fish, and other animals or artificial materials equivalent to those. Of these, a biological tissue material derived from mammals is preferable. Also, the "biological origin tissue" refers to tissue formed of the biological tissue material described above.

With the connective tissue body according to the present invention, a surface layer forming a surface of the connective tissue body includes a dense surface layer in which tissue is denser than a portion other than this surface layer. Dense tissue refers to a state in which collagen is dense in the connective tissue body. The dense surface layer, which is denser than the portion other than the surface layer, may be provided at least at a part of a surface of the connective tissue body. The surface of the connective tissue body formed by the dense surface layer (for example, the inner circumferential surface of a tubular structure described below) has high strength. In addition, the surface is dense, smooth, and has high strength, thereby resisting permeation by blood and lowering the possibility of thrombus formation. Moreover, the obtained connective tissue body is free of blood clots.

The term "surface layer" is not limited to the layer serving as the outer surface (outside surface) of the connective tissue body, and refers also to a layer inside the connective tissue body that forms a boundary surface to another member, such as a dissimilar member, present in the connective tissue body. Also, when the connective tissue body has a cavity therein, the boundary surface to the cavity is also considered as a surface layer.

That is, as will be described below, when a dissimilar member is embedded, a dense surface layer may be present at the boundary surface to the dissimilar member. In addition, when a hollow portion is provided inside, a dense surface layer may be present at the boundary surface to the hollow portion (for example, the inner circumferential surface of a tubular structure).

The connective tissue body according to the present invention preferably has, along its thickness direction, a dense surface layer and a portion other than a surface layer that is less dense than the dense surface layer. Providing a portion that is relatively sparse as compared with the dense surface layer increases the thickness, facilitates handling, and also increases the flexibility, so that the connective tissue body can easily conform when the whole tissue bends. The connective tissue body according to the present invention preferably has dense surface layers on opposite surfaces in the thickness direction, and a portion between the two dense surface layers that is less dense than the dense surface layers. With a tubular structure, for example, the thickness direction extends in a radial direction. Both of the surfaces at which dense surface layers are formed may be outside surfaces of the connective tissue body, both may be boundary surfaces to a cavity or a dissimilar material, or one of them may be an outside surface and the other may be a boundary surface.

To determine whether the surface layer of a connective tissue body has a dense surface layer, the connective tissue body is sliced into thin sections and stained with Masson's trichrome stain, and the stained connective tissue body is illuminated with a fixed illumination. The intensity values of the image thus obtained are used for the determination.

When the connective tissue body is stained with Masson's trichrome stain, collagen is stained blue, and dense tissue is stained dark. As such, when a sectioned connective tissue body is illuminated with a fixed illumination, a region with dense tissue has a lower intensity value than the other regions. A region of a lower intensity value is determined as a portion with high density.

That is, when the connective tissue body according to the present invention is photographed after Masson's trichrome staining, a surface layer with high density has a lower intensity value than a portion other than the surface layer in the photographed image, indicating the presence of a dense surface layer.

Using the fact that dense tissue has a low intensity value in a Masson's trichrome staining image, the present invention also determines the density of the surface layer of the connective tissue body.

The density obtained from the Masson's trichrome staining image may be defined as a tissue density representing the density of the tissue alone (that is, collagen). When a cross-section of a connective tissue body is observed by slicing it into thin sections, capillary vessel structures and voids (i.e., tissue-free areas) are typically observed. The tissue density is a density determined by removing such void sections through image processing.

In the present invention, the connective tissue body may be sliced into thin sections along the thickness direction, and the cross-section stained with Masson's trichrome stain may be observed to calculate the tissue density of the surface layer. Specifically, the ratio of the tissue density of the surface layer to the tissue density of the portion other than the surface layer (hereinafter, also referred to as a "tissue density ratio") is calculated along the thickness direction of the connective tissue body. The degree of denseness of the surface layer of the connective tissue body is thus determined.

The surface layer according to the present invention has a higher density than the portion other than the surface layer. Thus, the tissue density ratio of the surface layer is greater than 1, and preferably greater than or equal to 1.1, more preferably greater than or equal to 1.2. There is no limitation to the upper limit of the tissue density ratio, and it may be 3, or 2.5 under practical conditions.

In the present invention, when the tissue density ratio is greater than or equal to 1.1, collagen, particularly fibrous collagen, is densely present in the surface layer, increasing the strength. It is thus beneficially used in a living body. In addition, blood is less likely to permeate into the connective tissue body, lowering the possibility of thrombus formation.

In the present invention, the tissue density ratios of the surface layers at both surfaces may be within the above range, but the tissue density ratio of the surface layer at only one surface may be within the above range.

The dense surface layer according to the present invention has a higher tissue density than the other portion as described above and thus has a wall dissociation structure. The wall dissociation structure refers to a structure in which the dense surface layer is peeled off from the other portion as a layer when an end of the dense surface layer is pinched and peeled off with tweezers, for example.

When immersed in water, the dense surface layer has lower moisture content than the other portion. Specifically, when the weight of the dense surface layer separated by peeling and the weight of another layer are both B(g), and the weight of the dense surface layer or the other portion obtained after vacuum-drying at 25° C. for 12 hours is A(g), the moisture content of the dense surface layer defined by $(B-A)/A\times100$ is preferably less than 60%, more preferably less than 55%. In contrast, the moisture content of the other portion measured in the same manner is preferably greater than or equal to 60%, more preferably greater than or equal to 70%. As is clear from the low moisture content of the dense surface layer, the dense tissue can prevent blood permeation so that problems such as thrombus formation are less likely to occur. The moisture content may be obtained by calculating the average value of moisture contents measured at arbitrary multiple locations (e.g., ten locations) in the dense surface layer and in the other portion.

The connective tissue body according to the present invention has fibrous collagen as described above, and the fibrous collagen is preferably flat and smooth at the surface formed by the dense surface layer (for example, the inner circumferential surface of a tubular structure). The connective tissue body is assumed to resist blood permeation when the dense surface layer has flat fibrous collagen smoothly arranged at its surface and the tissue dense.

In contrast, in the portions other than the surface of the connective tissue body that is formed by a dense surface layer (e.g., the inner circumferential surface of a tubular structure), the fibrous collagen is arranged in a mesh pattern in an intersecting manner in both the dense surface layer and a sparse portion other than the dense surface layer. Specifically, bundles of fibrous collagen are oriented in one direction to form a layer, and the collagen bundles in this layer intersect the fibrous collagen bundles in another layer that are oriented in a different direction. These layers may be stacked to form a lamination structure with a mesh pattern. More than one such lamination structure may preferably be layered.

Also, in the portions other than the surface of the connective tissue body that is formed by a dense surface layer (e.g., the inner circumferential surface of a tubular structure), the fibrous collagen bundles may be thick in the dense surface layer and thinner in the portion other than the dense surface layer.

Similar to human collagen, the connective tissue body according to the present invention has a mesh structure and is thus suitable for regenerative medicine, which artificially regrows lost tissues and organs of a human body.

A condition in which fibrous collagen bundles are oriented in one direction is achieved when the fibrous collagen extends substantially in one direction. It is not necessary for the collagen fibers to be strictly parallel to one another.

The connective tissue body according to the present invention may have any shape, such as a tubular shape, a sheet shape, a rod shape, and a spherical shape. When formed in a tubular shape, the connective tissue body may be used as an artificial blood vessel, for example. When formed in a sheet shape, it may be used as a membranous tissue body, such as artificial pericardium, dura mater, skin, valve, cornea, diaphragm, or abdominal wall, or as a repairing material for a tubular or sac-shaped tissue body such as a blood vessel, esophagus, trachea, digestive tract, lymphatic vessel, or urinary duct, urethra, and urinary bladder. When formed in a rod shape, it may be used as a muscular tissue body such as a tendon or a ligament.

In addition to a tubular shape and a sheet shape, the connective tissue body may be formed in any shape for various organs, and may be formed in a shape corresponding to an artificial valve, for example. An artificial valve generally has a tubular portion and multiple valve leaflets bulging radially inward from the tubular portion.

Figure 2:
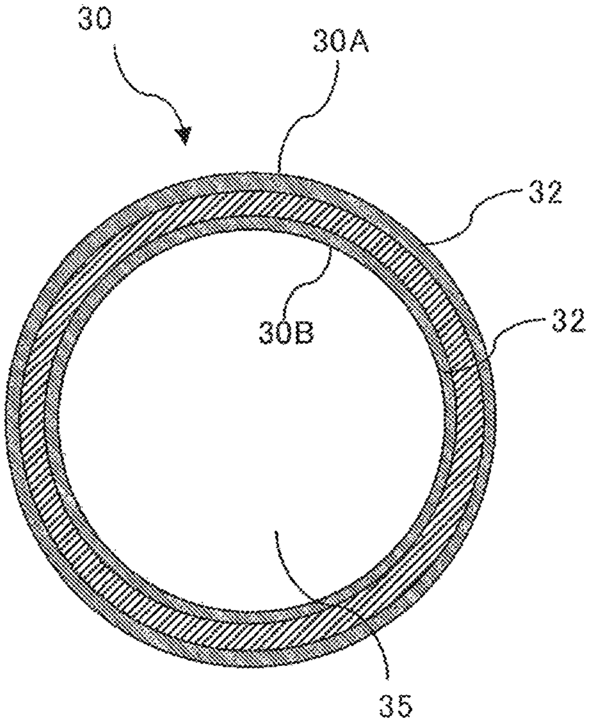
FIG. 2 is a schematic cross-sectional view showing an embodiment of a connective tissue body.

When a connective tissue body has a tubular portion (tubular structure), at least one of the two surfaces (i.e., the outer circumferential surface and the inner circumferential surface) has a dense surface layer. However, as shown in FIGS. 1 and 2, a connective tissue body 30 of tubular structure preferably has a dense surface layer 32 at least at its inner circumferential surface 30B. As shown in FIG. 2, it is also preferable to form dense surface layers 32 at both the inner circumferential surface 30B and the outer circumferential surface 30A.

Figure 3:
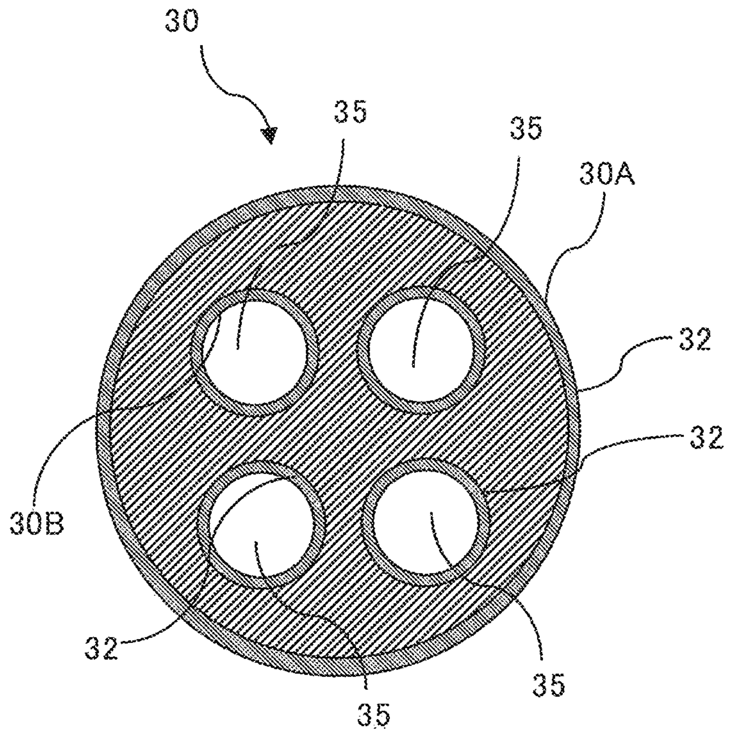
FIG. 3 is a schematic cross-sectional view showing an embodiment of a connective tissue body.

Also, as shown in FIGS. 1 and 2, a connective tissue body 30 of annular structure preferably has one hollow portion 35 therein, but may have multiple hollow portions 35 as shown in FIG. 3. As shown in FIG. 3, when multiple hollow portions 35 are provided, a dense surface layer 32 is preferably formed at the inner circumferential surface 30B of the tubular portion forming the rim of each hollow portion 35, and it is also preferable that dense surface layers 32 be formed at both the inner circumferential surfaces 30B and the outer circumferential surfaces 30A. Since the cylindrical tissue of high strength is embedded in flexible tissue, this connective tissue body can be used as a rod-shaped implant, such as a tendon or a ligament.

Figure 4:
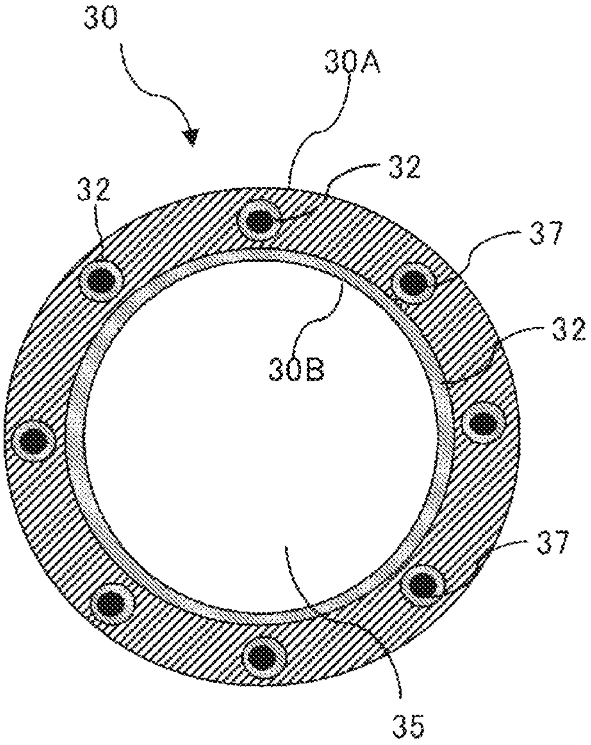
FIG. 4 is a schematic cross-sectional view showing an embodiment of a connective tissue body.
Figure 5:
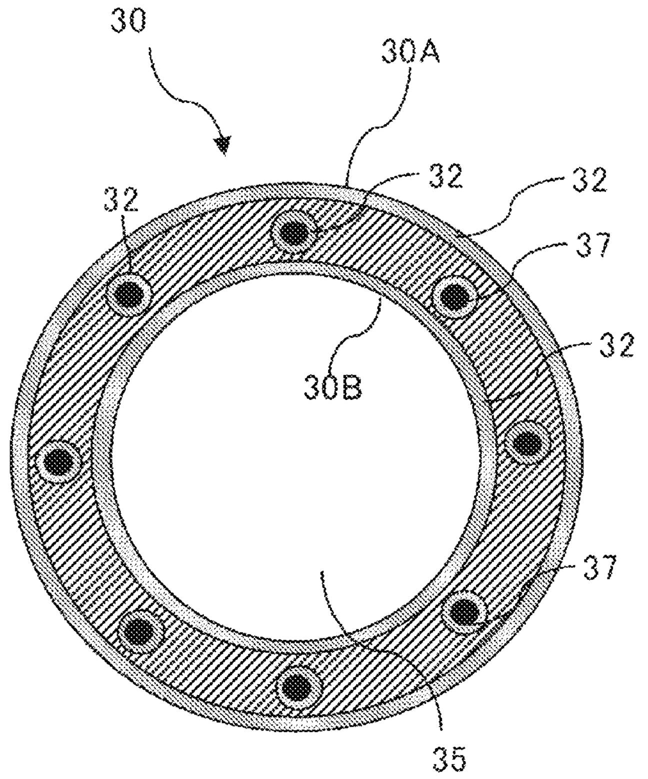
FIG. 5 is a schematic cross-sectional view showing an embodiment of a connective tissue body.

As shown in FIG. 4, a dissimilar member 37, which may be made of metal or polymer, may be embedded in a connective tissue body 30. As shown in FIG. 4, when a dissimilar member 37 is embedded, a dense surface layer 32 is preferably formed at the inner circumferential surface 30B of the tubular portion forming the rim of the hollow portion 35, and it is also preferable that dense surface layers 32 be formed at both the inner circumferential surface 30B and the outer circumferential surface 30A as shown in FIG. 5. As shown in FIGS. 4 and 5, in a connective tissue body 30 including a dissimilar member 37 embedded, the surface layers surrounding the dissimilar member 37 are also preferably formed as dense surface layers 32. When the surrounding portion bordering the dissimilar member 37 is a dense surface layer 32, the dissimilar member 37 is firmly fixed in the tissue while maintaining a certain degree of mobility inside the flexible tissue. As such, the dissimilar member 37 is stabilized and thus not internally displaced.

A stent is preferably used as the dissimilar member 37. The connective tissue body 30 with an embedded stent can be used as a tubular implant, follow large deformation without damaging the whole tissue, and contract and expand.

In addition to an expandable, deformable stent, examples of the dissimilar member 37 include linear, ring-shaped, and spiral structures.

Also, the dissimilar member 37 may be made of a metal having biocompatibility, a polymer material, or a biological origin material, for example. Examples of metal include stainless steel, titanium, cobalt chrome alloy, nickel titanium alloy, and magnesium alloy. These metals can be suitably used for stents, for example. Examples of polymer material include resins such as nylon resin, polyether ether ketone (PEEK) resin, silicone resin, acrylic resin, fluorocarbon resin, urethane resin, ethylene resin, styrene resin, and propylene resin. These polymer materials may coat the surface of metal. Examples of biological origin material include inorganic materials, such as hydroxyapatite, and organic materials mainly composed of cellular components such as cartilage.

When a connective tissue body of tubular structure is used as an artificial blood vessel or an artificial valve as described above, blood flows inside the connective tissue body. When a dense surface layer is formed at the inner circumferential surface, the dense surface layer helps to prevent the blood flowing inside from permeating into the connective tissue body, lowering the possibility of thrombus formation in the artificial blood vessel, artificial valve, or the like.

When the connective tissue body is sheet-shaped, a dense surface layer may be formed at one surface of the sheet-shaped connective tissue body, but a dense surface layer may be formed on each surface.

[Method for Producing Connective Tissue Body] The connective tissue body according to the present invention can be produced using a connective tissue body formation substrate and by an encapsulation reaction. Specifically, it can be produced subcutaneously in a living body by a production method including the following steps.

Step 1: A step of placing, in a living body, a connective tissue body formation substrate including a tissue formation surface that is at least partially made of a polymer material Step 2: A step of removing air percutaneously and transluminally from a space in the living body in which the connective tissue body formation substrate is placed to the outside of the living body Step 3: A step of allowing a connective tissue body to form on the tissue formation surface Step 4: A step of removing, from the living body, the connective tissue body formation substrate on which the connective tissue body is formed Step 5: A step of peeling off the connective tissue body from the connective tissue body formation substrate Connective Tissue Body Formation Substrate First, the connective tissue body formation substrate used in the above-mentioned production method is described.

The surfaces of the connective tissue body formation substrate include tissue formation surfaces for allowing a connective tissue body to form. The tissue formation surfaces are preferably configured to define a space (tissue formation space) according to the shape of the connective tissue body. For example, the connective tissue body formation substrate may have at least a pair of mutually opposed tissue formation surfaces, and a connective tissue body may be formed by an encapsulation reaction in the tissue formation space between the pair of tissue formation surfaces.

The connective tissue body formation substrate may be made of a material that has sufficient strength to resist significant deformation in an environment where a biological tissue material is present, such as in a living body, has chemical stability, is resistant to impacts such as sterilization, and releases no or little substance that irritates the living body.

Specifically, the connective tissue body formation substrate is made of a polymer material, a metal material, or the like. Specific examples of preferable polymer material include materials used for components of medical devices to be retained in the body, such as nylon resin, PEEK resin, silicone resin, acrylic resin, fluorocarbon resin, urethane resin, ethylene resin, styrene resin, and propylene resin. Specific examples of preferable metal material include materials used for components of medical devices to be retained in the body, such as stainless steel, titanium, cobalt chrome alloy, nickel titanium alloy, and magnesium alloy.

The tissue formation surface is at least partially made of a polymer material such as resin, preferably a material used for components of medical devices to be in contact with the body, such as nylon resin, PEEK resin, silicone resin, acrylic resin, fluorocarbon resin, urethane resin, ethylene resin, styrene resin, or propylene resin. A biological tissue material tends to accumulate densely on a surface of these resins, facilitating the formation of a dense surface layer. Thus, when the connective tissue body formation substrate has a pair of mutually opposed tissue formation surfaces, one of the tissue formation surfaces is preferably made of a polymer material such as resin, and more preferably a material used for components of medical devices to be retained in the body, such as nylon resin, PEEK resin, silicone resin, acrylic resin, fluorocarbon resin, urethane resin, ethylene resin, styrene resin, and propylene resin. The other tissue formation surface is preferably made of a metal material.

When the tissue formation surface is made of a polymer material or a metal material described above, the entire component including the tissue formation surface may be made of the polymer material or the metal material, or only the tissue formation surface may be made of the polymer material or the metal material. For example, the tissue formation surface may be made of a polymer material by coating the surface of a metal component with the polymer material.

The shape of the connective tissue body formation substrate may be designed according to the connective tissue body to be formed. For example, to form a tubular connective tissue body, the connective tissue body formation substrate 10 may include a cylindrical cover member 11 and a core member 12 inserted in the cover member 11 as shown in FIG. 6.

Figure 6:
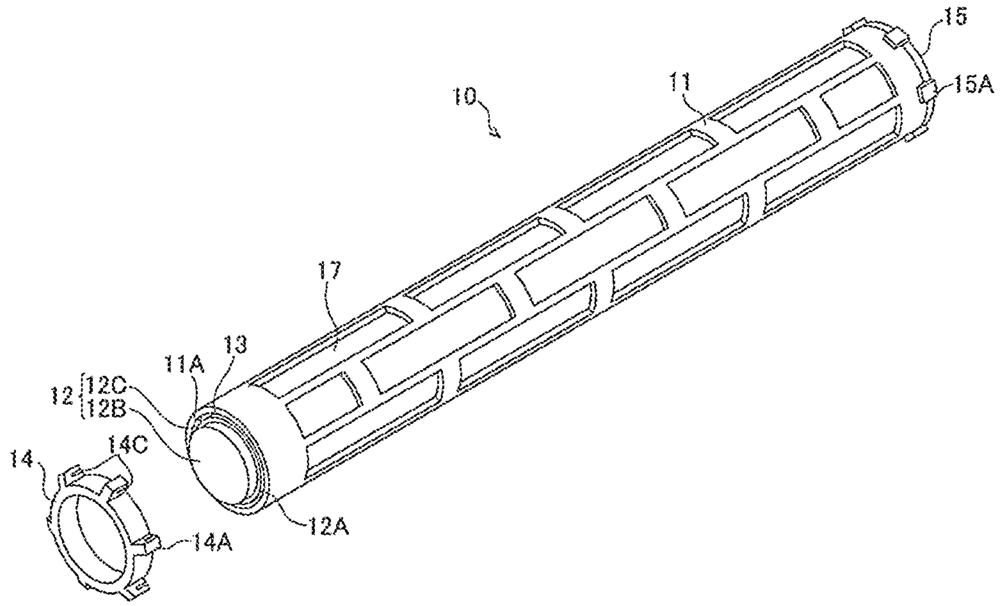
FIG. 6 is a perspective view showing an embodiment of a connective tissue body formation substrate.

With the connective tissue body formation substrate 10 shown in FIG. 6, the inner circumferential surface of the cover member 11 forms one tissue formation surface 11A, and the outer circumferential surface of the core member 12 forms the other tissue formation surface 12A. The tissue formation surfaces 11A and 12A define a tissue formation space 13 between them. The cover member 11 has holes 17 connecting the tissue formation space 13 and the outside of the substrate to each other. The cover member 11 typically has multiple holes 17.

At the opposite end surfaces of the cover member 11, lids 14 and 15 are provided to close the respective ends of the tissue formation space 13. The lids 14 and 15 are annular and have locking portions 14A and 15A on their outer circumferences. Each lid 14, 15 has multiple locking portions 14A, 15A. Each locking portion 14A has a groove 14C into which one end of the cover member 11 is fitted. Each locking portion 15A also has a groove (not shown) in the same manner. The ends of the core member 12 are fitted into the inside of the annular lids 14 and 15, and the ends of the cover member 11 are fitted into the grooves of the locking portions 14A and 15A. The lids 14 and 15 thus couple and fasten the cover member 11 and the core member 12 to each other.

There is no limitation to the holes 17, and the holes 17 may be circular, elliptical, or slits. When the holes 17 are circular or elliptical, to facilitate the entry of connective tissue and biological tissue materials, the diameter of the circular or elliptical holes is preferably greater than or equal to 1 mm and less than or equal to 10 mm.

The holes 17 are preferably slits as shown in FIG. 6. When the holes 17 are slits, the holes 17 will not be closed by connective tissue, facilitating the entry of connective tissue into the tissue formation space 13. The slit may have a slit width of greater than or equal to 1 mm, which facilitates the entry of connective tissue and biological tissue materials. For example, the slit width may be less than or equal to 10 mm. Typically, the length of the slit is preferably greater than twice the slit width, preferably less than five times, and more preferably less than three times.

The area ratio of the slits to the tissue formation surface 11A of the cover member 11 may be set to less than or equal to ⅔. A smaller area ratio of the slits results in a more desirable surface condition of the connective tissue body surface formed on the tissue formation surface 11A. Also, to allow the connective tissue and biological tissue materials to enter the tissue formation space 13 through the slits, the area ratio of the slits to the tissue formation surface 11A of the cover member 11 is preferably greater than or equal to 1/10. When the holes are a different shape than slits, such as circular or elliptical holes, the area ratio of the holes to the tissue formation surface 11A of the cover member 11 is also preferably greater than or equal to 1/10 and less than or equal to ⅔.

The slits may be arranged such that the longitudinal direction of the slits is parallel to the central axis of the substrate as shown in FIG. 6, but the slits may be arranged such that the longitudinal direction of the slits is inclined with respect to the central axis of the substrate. Multiple slits may be arranged in the circumferential direction and in the longitudinal direction.

The outer circumferential surface of the core member 12 is preferably made of a polymer material such as the above-mentioned resin, particularly nylon resin, PEEK resin, silicone resin, or acrylic resin. This facilitates the formation of a dense surface layer at the inner circumferential surface of the tubular connective tissue body according to the present invention. For example, the core member 12 may include a center member 12B and a cover tube 12C covering the outer circumferential surface of the center member 12B, and the cover tube 12C may be made of the above-mentioned polymer material.

In contrast, the cover member 11 is preferably made of a metal material, and its tissue formation surface 11A (that is, the inner circumferential surface) is preferably made of a metal material. Compared with the above-mentioned polymer material, a metal material resists the accumulation of a biological tissue material on its surface, preventing an early closure of the holes 17 of the cover member 11 by the biological tissue material. Accordingly, the biological tissue material accumulates in the tissue formation space 13 over a long period of time. Nevertheless, the cover member 11 may be formed of the above-mentioned polymer material. When the cover member 11 is made of a polymer material, dense surface layers are formed at both the outer and inner circumferential surfaces of the tubular connective tissue body as shown in FIG. 2.

Figure 7:
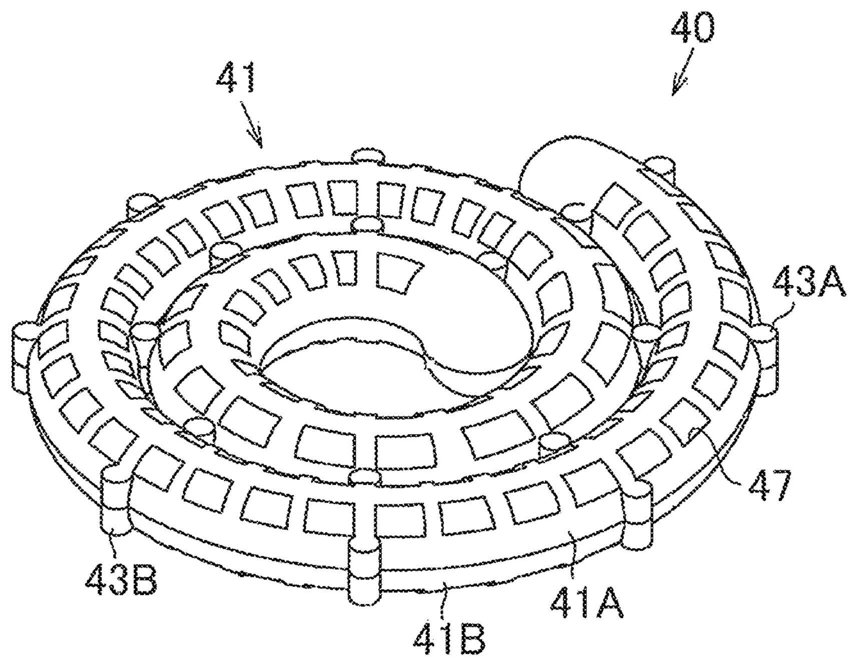
FIG. 7 is a perspective view showing an embodiment of a connective tissue body formation substrate.
Figure 8:
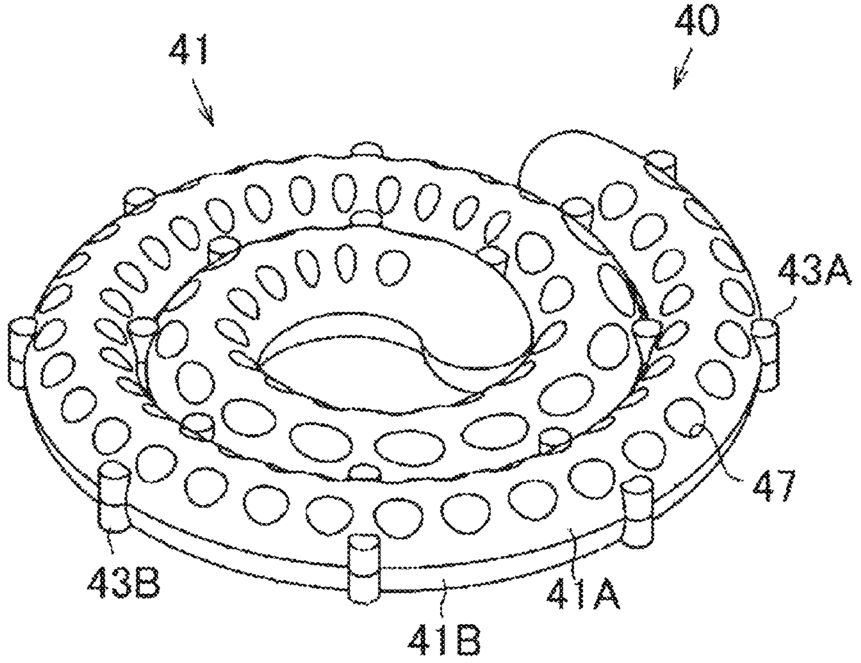
FIG. 8 is a perspective view showing an embodiment of a connective tissue body formation substrate.

The connective tissue body formation substrate is not limited to a linear shape and may have various shapes, such as a curved shape. As shown in FIGS. 7 and 8, it may be a connective tissue body formation substrate 40 with two or more annular sections wound in a spiral shape.

As shown in FIGS. 7 and 8, the connective tissue body formation substrate 40 includes a cover member 41. The cover member 41 has two or more annular sections wound in a spiral shape. The cover member 41 may include an upper member 41A and a lower member 41B, which may be vertically separated. These members are abutted against each other, forming a tubular structure. The upper member 41A and the lower member 41B include coupling members 43A and 43B, respectively, which are coupled to fasten these members 41A and 41B together. The cover member 41 may have multiple holes 47, which may be arranged in the circumferential direction and the longitudinal direction. The holes 47 may be rectangular as shown in FIG. 7, circular as shown in FIG. 8, or have other shapes.

Figure 9:
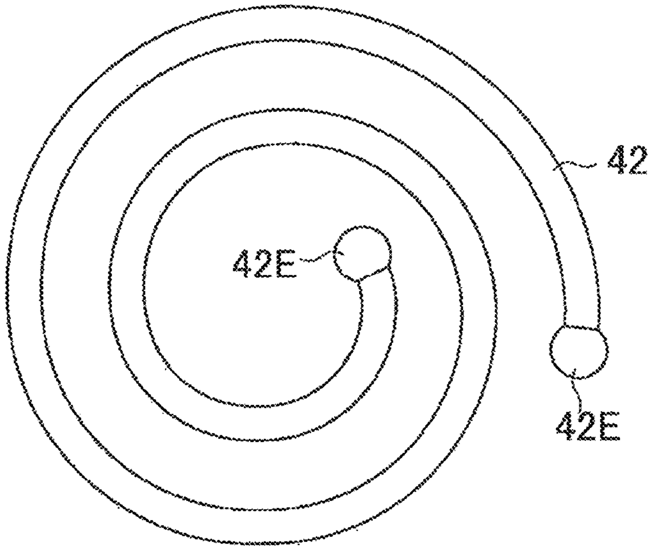
FIG. 9 is a perspective view showing an embodiment of a core member.

A core member 42 is arranged inside the cover member 41 (see FIG. 9). As shown in FIG. 9, the core member 42 has two or more annular sections wound in a spiral shape in accordance with the shape of the cover member 41. The two ends 42E and 42E of the core member 42 have a larger width and height than the other portion, and have a spherical shape, for example. Such a shape allows, when the ends of the cover member 41 have recesses, for example, the ends 42E and 42E to be fitted into these recesses, fastening the core member 42 to the cover member 41. However, the ends of the core member 42 are not limited to this configuration.

In the connective tissue body formation substrate 40, a tissue formation space is formed between the inner circumferential surface of the cover member 41 and the outer circumferential surface of the core member 42. The inner circumferential surface of the cover member 41 and the outer circumferential surface of the core member 42 may be made of materials described above.

A connective tissue body is formed in the tissue formation space as described above also when the connective tissue body formation substrate 40 shown in FIGS. 7 to 9 is used. The connective tissue body formation substrate 40 is suitable to form a connective tissue body for an artificial blood vessel, for example, because it has two or more annular sections and thus forms a connective tissue body of a long tubular structure.

Figure 10:
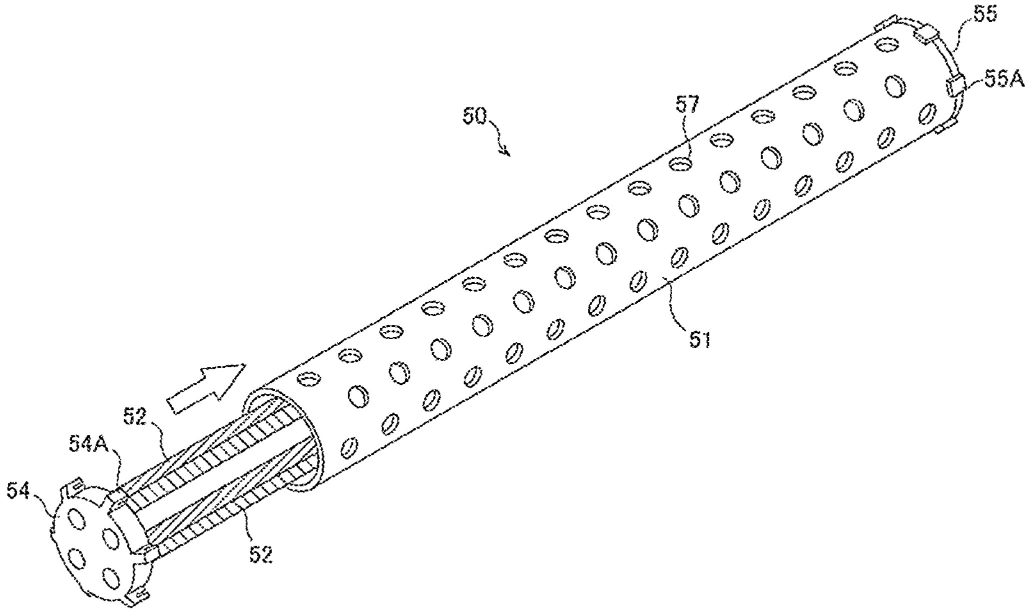
FIG. 10 is a perspective view showing an embodiment of a connective tissue body formation substrate.

The number of core members does not have to be one, and two or more core members may be provided. FIG. 10 shows a specific example of a connective tissue body formation substrate 50 having two or more core members. The connective tissue body formation substrate 50 includes a cover member 51 formed by a cylindrical member and multiple core members 52 inserted in the cover member 51. The core members 52 may be attached to lids 54 and 55. The lids 54 and 55 include multiple locking portions 54A and 55A as described above. For example, the end portions of the cover member 51 are fitted into the grooves of the locking portions 54A and 55A. The lids 54 and 55 thus couple and fasten the cover member 51 and the core members 52 together.

When multiple core members 52 are provided, each core member 52 may have a rod shape and a thickness of 0.2 to 3 mm, preferably 0.5 to 2.5 mm, for example. The maximum cross-sectional area of the core members 52 in the interior space of the cover member 51 may be about 20 to 60%, for example. The maximum cross-sectional area is the cross-sectional area of the section that is perpendicular to the axis of the connective tissue body formation substrate 50 and has the largest area.

As illustrated in FIG. 10, the cover member may have multiple circular holes 57, but there is no limitation to the configuration of the holes 57. They may be any holes described above or slits. Also, although FIG. 10 illustrates the circular holes 57 in a staggered arrangement, there is no limitation to the arrangement, and any arrangement may be used.

Figure 11:
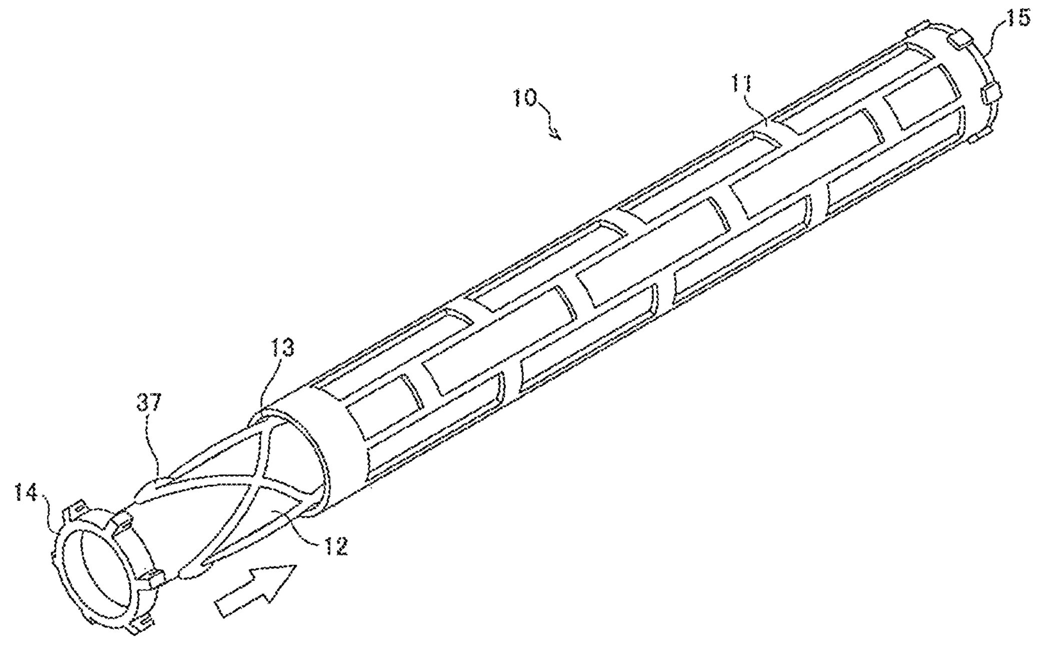
FIG. 11 is a perspective view showing an embodiment of a connective tissue body formation substrate.

When a dissimilar member is embedded in the connective tissue body, the dissimilar member may be arranged in the tissue formation space. For example, as shown in FIG. 11, for a connective tissue body formation substrate having a core member 12 and a cover member 11, a dissimilar member 37 may be arranged in the tissue formation space 13 between the core member 12 and the cover member 11. However, the dissimilar member 37 is preferably not in close contact with the core member 12 or the cover member 11. By avoiding close contact with the core member 12 and the cover member 11, the biological origin tissue enters between the dissimilar member 37 and the core member 12 or the cover member 11. This facilitates the formation of dense surface layers 32 over the entire inner circumferential surface 30B and the outer circumferential surface 30A of the connective tissue body 30 as shown in FIG. 5. The dissimilar member 37 forms a part of the connective tissue body formation substrate, and its surface may serve as a tissue formation surface.

Figure 12:
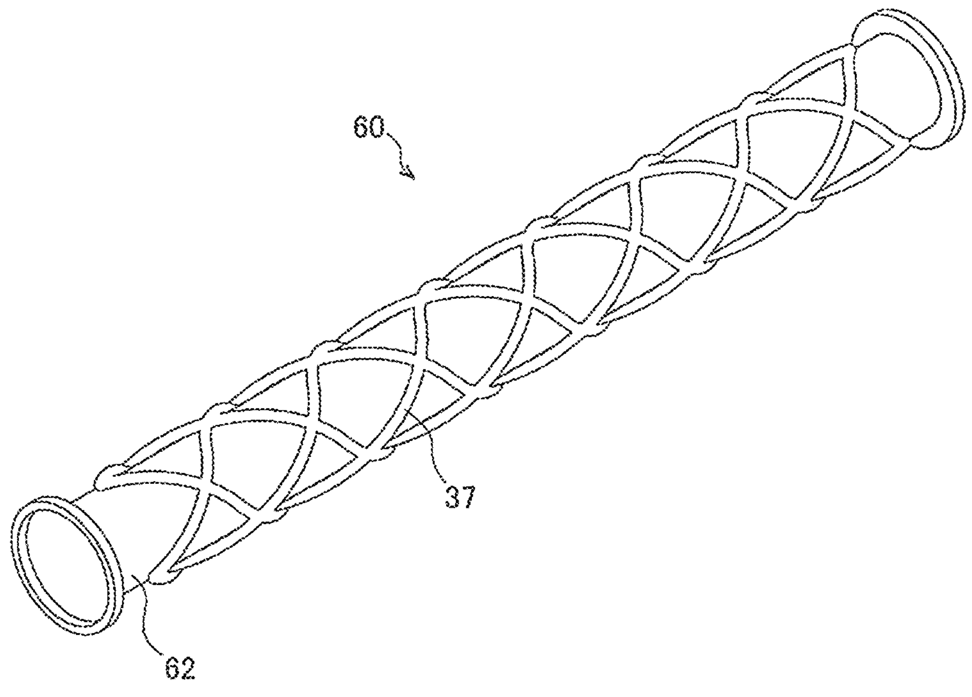
FIG. 12 is a perspective view showing an embodiment of a connective tissue body formation substrate.

To form a tubular connective tissue body, the connective tissue body formation substrate does not have to include a cover member and a core member. For example, the cover member may be omitted. FIG. 12 shows an example of a connective tissue body formation substrate 60 in which the cover member is omitted. Even when the cover member is omitted, the surface of the core member 62 serves as a tissue formation surface, and a connective tissue body is formed on the surface of the core member 62 by an encapsulation reaction. In the connective tissue body formation substrate 60 in which the cover member is omitted, a dissimilar member 37 may also be arranged on the outer circumferential surface of the core member 62 as shown in FIG. 12. The dissimilar member 37 is preferably not in close contact with the outer circumferential surface of the core member 62 as described above. As shown in FIG. 12, when the dissimilar member 37 is arranged in the tissue formation space 13 and the cover member is not provided, the connective tissue body 30 as shown in FIG. 4 may be obtained.

FIGS. 11 and 12 show examples in which the dissimilar member 37 is a stent. The stent may be attached to the outer circumferential surface of the core member 62 by expanding its diameter, for example. It should be understood that the dissimilar member 37 is not limited to a stent, and other materials may be used.

To produce a sheet-shaped connective tissue body, a connective tissue body formation substrate that includes two opposed planar members may be used. In this case, the opposed surfaces of the two planar members may serve as tissue formation surfaces, and biological tissue materials may accumulate in the tissue formation space between this pair of tissue formation surfaces to form a connective tissue body.

Here, one of the two tissue formation surfaces is preferably made of a polymer material such as the above-mentioned resin, particularly nylon resin, PEEK resin, silicone resin, or acrylic resin. These polymer materials facilitate the formation of a dense surface layer on the tissue formation surface. Also, one of the two planar members may have holes, such as slits. Furthermore, it is preferable that the tissue formation surface of one of the planar members be made of the above-mentioned polymer material and the other planar member have holes. The tissue formation surface of the planar member with holes is preferably made of a metal material.

To produce an artificial valve, for example, the connective tissue body formation substrate has a core member and a cover member, into which the core member is inserted. The outer circumferential surface of the core member and the inner circumferential surface of the cover member serve as tissue formation surfaces, and a tissue formation space is defined between this pair of tissue formation surfaces. The tissue formation space may be defined so as to have a shape corresponding to an artificial valve or an artificial valve precursor that can be made into an artificial valve by appropriate processing. For example, the tissue formation space may be defined according to the shape of an artificial valve that includes a tubular portion and multiple valve leaflets bulging radially inward from the tubular portion, or a precursor of this artificial valve.

The outer circumferential surface of the core member is preferably made of a polymer material such as the above-mentioned resin, particularly nylon resin, PEEK resin, silicone resin, or acrylic resin. This facilitates the formation of a dense surface layer at the inner circumferential surface of the artificial valve. Also, the cover member preferably has holes such as slits, and its inner circumferential surface is preferably made of a metal material.

The steps of the above-mentioned method for producing a connective tissue body are now described.

Step 1

In step 1, a connective tissue body formation substrate is placed in a living body. Examples of living bodies include humans and other non-human mammals such as dogs, cows, pigs, goats, rabbits, and sheep, birds, fish, and other animals. Of these, mammals are preferable. The space where the connective tissue body formation substrate is placed in the living body may be a space under the skin or in a peritoneal cavity.

A method of placing a connective tissue body formation substrate in a living body may include performing a minimal incision surgery, forming an insertion opening in the surface of the living body, and implanting the connective tissue body formation substrate in the animal through the insertion opening. After the implantation, the incision is sutured. Examples of preferable locations for the implantation of the connective tissue body formation substrate include a peritoneal cavity having a volume for receiving the connective tissue body formation substrate, and a space under the skin in a limb, shoulder, back, or abdomen, for example. Specifically, for subcutaneous implantation, the substrate is preferably implanted in a space between the lower side of the dermic layer and the upper side of the fat layer or the muscle layer. More specifically, the substrate may be placed in a subcutaneous pocket in the living body prepared with sufficient hemostasis between the lower side of the dermic layer and the upper side of the fat layer or the muscle layer.

Also, the implantation is preferably performed in a minimally invasive manner and by performing a minimal incision surgery under sufficient anesthesia. Bleeding should be minimized, and sufficient hemostasis is required if bleeding occurs. The subcutaneous pocket preferably has a larger space than the connective tissue body formation substrate to be placed. By creating peeled surfaces under the skin larger than the substrate, the biological reaction is enhanced, producing a synergistic effect with the repair and curing of the peeled surfaces. This promotes the formation of tissue inside the substrate.

Specifically, an insertion opening is first formed in the surface of the living body, layers in the body are peeled off from each other through the insertion opening to form a pocket under the skin. The in vivo connective tissue body formation substrate is inserted through the insertion opening and placed in the living body. The insertion opening is sutured or otherwise closed.

Figure 13:
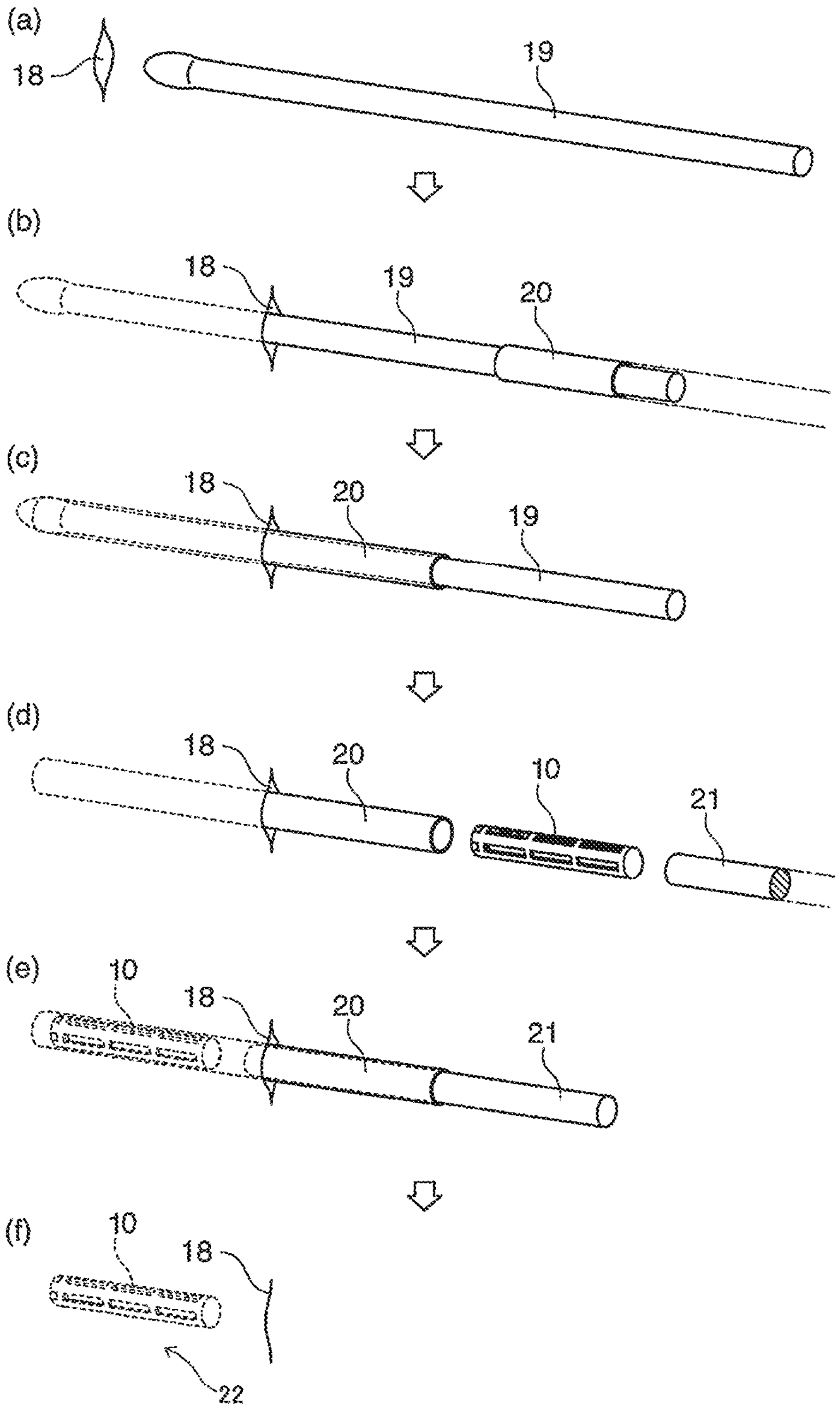
FIG. 13 shows an embodiment of a process of placing a connective tissue body formation substrate in a living body.

A guide rod may be used to facilitate the placement of the connective tissue body formation substrate in the living body while reducing subcutaneous bleeding. As shown in FIG. 13, an insertion opening 18 is first formed in the surface of the living body, and the distal end of a guide rod 19 having a convex tip is inserted into the living body through the insertion opening 18 (the state (a) in FIG. 13). Then, an insertion tube 20 is slid over the outer side of the guide rod 19 into the living body through the insertion opening 18 (the states (b) and (c) in FIG. 13). After inserting the insertion tube 20, the guide rod 19 is pulled out. Then, a connective tissue body formation substrate 10 is inserted into the insertion tube 20 (the state (d) in FIG. 13) and pushed in with a push rod 21 (the state (e) in FIG. 13). The insertion tube 20 is then pulled out through the insertion opening 18, placing the connective tissue body formation substrate 10 in the living body. After the insertion tube 20 is pulled out, the insertion opening 18 is sutured or otherwise closed (the state (f) in FIG. 13). It is desirable also in this example that the subcutaneous pocket provide a larger space than the substrate. When the guide rod has a larger outer diameter than the substrate, larger peeled surfaces are formed. This enhances the biological reaction, producing a synergistic effect with the repair and curing of the peeled surfaces. The tissue formation is thus promoted in the substrate, forming a dense collagen layer particularly at the surface in contact with the substrate.

Step 2

After the completion of step 1, air is removed from the space 22 in the living body in which the connective tissue body formation substrate 10 is placed. Any method may be used as long as it removes air percutaneously and transluminally to the outside of the living body. For example, the air may be removed by inserting the tip of a syringe into the space 22 from the outside of the living body. The degree of vacuum is preferably in the range of 0.1 to 0.5 atm. Merely pressing from the outside of the skin only results in close contact between the substrate and the subcutaneous tissue, causing the skin cells to move closer to the substrate surface. By further forming a vacuum within the substrate, the skin cells are drawn into the substrate, facilitating the formation of tissue within the substrate. Thus, a dense collagen layer is formed particularly at the surface in contact with the substrate.

Step 3

After the air is removed in step 2, the connective tissue body formation substrate 10 is left in the living body for a predetermined duration. This duration of placement differs depending on the type of the living body, but it may be left for a long period of time as long as it is at least 20 days in which the tissue is formed. A longer duration hardly affects the shape of the formed tissue. For example, the duration may be 20 to 90 days, preferably 30 to 60 days. By leaving for the predetermined duration, a connective tissue body is formed in the tissue formation space of the connective tissue body formation substrate 10.

The present production method removes air from the space 22 in step 2, allowing tissue in the living body to adhere to the outer circumferential surface of the connective tissue body formation substrate 10. This facilitates the accumulation of connective tissue and biological tissue materials in the tissue formation space. In addition, since the tissue formation surface is at least partially made of a polymer material, the connective tissue and the biological tissue materials densely accumulate on the tissue formation surface made of the polymer material. The present production method thus forms the above-mentioned dense surface layer on the tissue formation surface made of a polymer material.

In addition, the connective tissue body formed on the tissue formation surface made of a polymer material increases the likelihood that flat collagen is smoothly arranged at its outermost surface. Moreover, in the portion of the dense surface layer other than the outermost surface, and the portion that is further inward, connective tissue accumulates moderately, and the fibrous collagen is more likely to be arranged in a mesh pattern in an intersecting manner. This helps to form a configuration in which lamination structures are layered as described above.

Step 4

In step 4, the connective tissue body formation substrate on which the connective tissue body is formed in step 3 is removed from the living body. Specifically, an opening for removal is formed in the position of the biological surface where the connective tissue body formation substrate is implanted in the living body, and the connective tissue body formation substrate may be removed through this opening.

For example, when the connective tissue body formation substrate has an attachment portion (not shown) formed by a thread portion (e.g., an external thread), the attachment portion is engaged with a thread portion (e.g., an internal thread) provided at the tip of a substrate removal tool. The connective tissue body formation substrate is thus attached to the tip of the substrate removal tool so that the connective tissue body formation substrate is removed from the living body.

Alternatively, an end of the connective tissue body formation substrate may be pinched and secured with forceps to be removed from the living body.

Step 5

Figure 14:
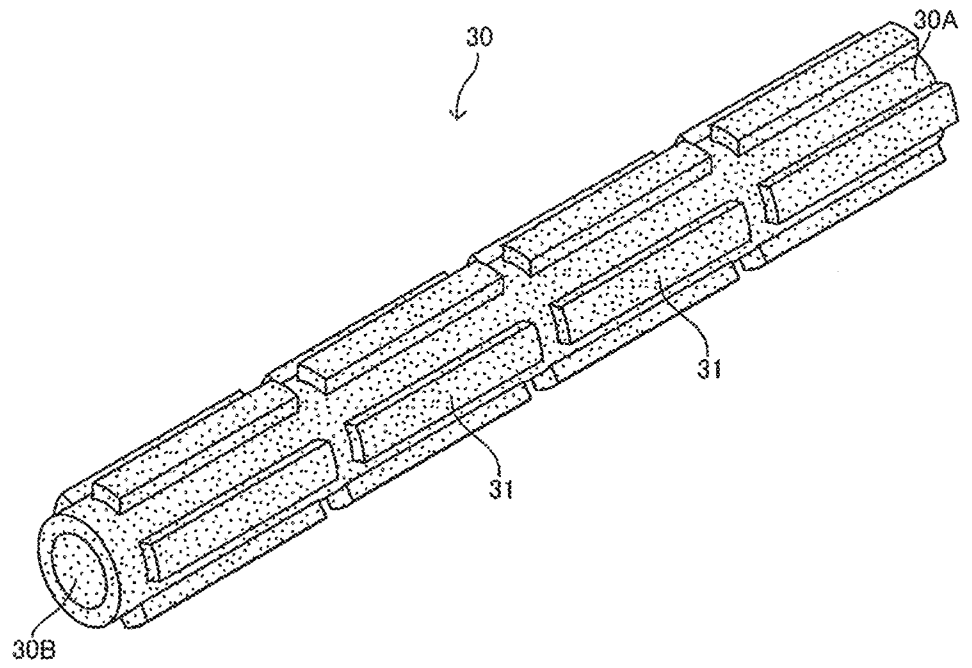
FIG. 14 is a perspective view showing an embodiment of a connective tissue body.

Then, the connective tissue body formed in the tissue formation space is peeled off from the tissue formation surfaces after breaking the connective tissue body formation substrate if necessary, thereby obtaining the connective tissue body. When the connective tissue body formation substrate includes a cover member 11 with holes 17 formed by slits and a core member 12 as shown in FIG. 6, the connective tissue body is a tubular connective tissue body 30 as shown in FIG. 14. The outer circumferential surface 30A of the connective tissue body 30 has multiple ridges 31 formed corresponding to the slits, and the inner circumferential surface 30B of the connective tissue body 30 has a dense surface layer.

When the obtained connective tissue body is xenotransplanted, a process for removing immunogens, such as decellularization, dehydration, or immobilization, is preferably performed to prevent rejection after the transplantation.

The production method described above is an example, and the method is not limited to this example. For example, a method for placing a connective tissue body formation substrate in a living body is specifically described with reference to the drawings, but the present disclosure is not limited to the specific examples.

Also, although the method described above produces a connective tissue body in vivo, a connective tissue body does not have to be produced in vivo. For example, a connective tissue body may be produced in the same or similar environment as in a living body.

In this case, a connective tissue body formation substrate may be appropriately placed in an environment where a biological tissue material is present, and a connective tissue body may be formed in the tissue formation space in the same manner as described above. A part of the tissue formation surface that defines the tissue formation space is made of a polymer material. In addition, biological tissue or the like may be brought into close contact with the outer circumferential surface of the connective tissue body formation substrate to facilitate the formation of a dense surface layer on the tissue formation surface made of a polymer material.

EXAMPLES

The present invention is now described in further detail using examples, but the present invention is not limited to these examples. Unless otherwise specified, "%" refers to "mass %" in the following description.

A method for measuring the density of a surface layer is now specifically described.

[Density Measurement]

Section Preparation

Paraffin-embedded blocks were prepared from the connective tissue bodies obtained in examples and comparative examples by the following procedure 1) to 7).

1) The connective tissue body was immersed in a 4% paraformaldehyde phosphate buffer solution for 24 hours.
2) The connective tissue body was removed and then immersed in 70% ethanol.
3) The process of immersing the connective tissue body in 99.5% ethanol for 30 minutes and removing was performed five times.
4) The connective tissue body was immersed in 100% ethanol for 30 minutes.
5) The process of immersing the connective tissue body in xylene for 30 minutes and removing was performed twice.
6) The process of immersing the connective tissue body in paraffin dissolved at 60° C. for 30 minutes and removing was performed four times.
7) The block was placed in a mold for embedding, and paraffin was poured into the mold and solidified to form the block.

The paraffin-embedded block was sliced to a thickness of 3 μm to prepare sections. The connective tissue body was sliced in the thickness direction. The sections were then deparaffinized. The deparaffinization was performed by immersing the sections in xylene twice, in 100% ethanol twice, in 70% ethanol once, and in distilled water once for 10 minutes each.

Masson's Trichrome Staining

Then, Masson's trichrome staining was performed according to the following procedure 1) to 21).

1) The sections were immersed in a mordant solution (manufactured by Muto Pure Chemicals Co., Ltd., product number "40061") for 30 minutes.
2) The sections were removed from the mordant and rinsed with running water.
3) The sections were immersed in a mixed solution of equal parts of iron hematoxylin solution (Weigert's iron hematoxylin solution 1 (Muto Pure Chemicals Co., Ltd., product number "40341")) and Weigert's iron hematoxylin solution 2 (Muto Pure Chemicals Co., Ltd., product number "40351") for 10 minutes.
4) The sections were removed from the mixed solution and rinsed with running water.
5) The sections were cleaned by shaking vertically for a few seconds in 1% hydrochloric acid alcohol about five times. The 1% hydrochloric acid alcohol was obtained by diluting hydrochloric acid with 70% ethanol so as to have a concentration of 1%.
6) The sections were rinsed with running water for 10 minutes for color development.
7) The sections were immersed in a second mordant (manufactured by Muto Pure Chemicals Co., Ltd., product number "81411") for 30 seconds.
8) The sections were removed from the second mordant and rinsed with running water for 1 minute.
9) The sections were shaken vertically for a few seconds in 1% acetic acid solution about five times.
10) The sections were immersed in 0.75% orange G (manufactured by Muto Pure Chemicals Co., Ltd., product number "40231") for 1 minute.

11) The sections were removed from the orange G and cleaned by shaking vertically for a few seconds in 1% acetic acid solution about five times.

12) The sections were immersed in Masson stain B (manufactured by Muto Pure Chemicals Co., Ltd., product number "40251") for 20 minutes.

13) The sections were cleaned by shaking vertically for a few seconds in 1% acetic acid solution about five times.

14) The sections were immersed in a 2.5% phosphotungstic acid solution (manufactured by Muto Pure Chemicals Co., Ltd., product number "40181") for 30 minutes.

15) The sections were removed from the phosphotungstic acid solution and then cleaned by shaking vertically for a few seconds in 1% acetic acid solution about five times.

16) The sections were immersed in aniline blue solution (manufactured by Muto Pure Chemicals Co., Ltd., product number "40201") for 30 minutes.

17) The sections were removed from the aniline blue solution and then cleaned by shaking vertically for a few seconds in 1% acetic acid solution about five times.

18) The sections were cleaned by shaking vertically for a few seconds in 100% ethanol about ten times.

19) The sections were immersed in 100% ethanol for 5 minutes to dehydrate.

20) The sections were immersed in xylene for 5 minutes and then removed from xylene. This process was repeated three times.

21) A mounting medium (Entellan™new Millipore, 1.07961.0100, manufactured by Merck KGaA) was applied to the sections in drops, and cover glasses were placed on the sections. The mounting medium was solidified on the glasses to enclose the sections.

Image Observation

Each section enclosed in the mounting medium as described above was illuminated with a transmission Koehler illumination attached to a microscope (manufactured by Nikon Corporation, trade name "ECLIPSE E1000") with an illuminance of 500 lx and observed under a magnification of 10 times, and 30 images were captured.

For each image, image analysis was performed according to the following procedure 1) to 8) to calculate the tissue density ratio.

1) The blue part (collagen part) was extracted by the H filter of the HSV space.

Figure 22:
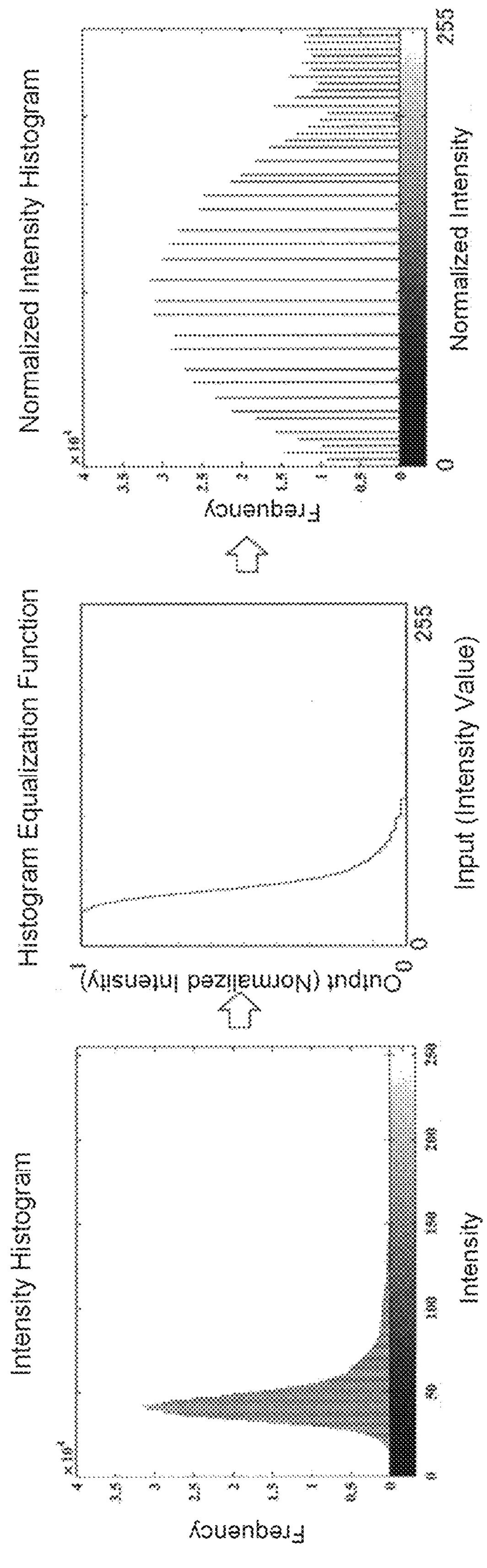
FIG. 22 shows the intensity distribution data of Example 1 after equalization.

2) The intensity values were calculated by grayscale conversion (256 gradations). FIG. 22 shows histograms of the intensity values of Example 1, which will be described below, as intensity histograms.

3) Histogram equalization was performed using the histogram equalization function to distribute the intensity values while performing enhancing processing to obtain a normalized intensity histogram (see FIG. 22). The intensity values were inverted, and the portion with the highest intensity (that is, the portion with the lightest staining) was defined as 0, and the portion with the lowest intensity (i.e., the portion with the darkest staining) was defined as 1.

4) Intensity data along an arbitrary straight line L (see FIG. 16) in the thickness direction of the connective tissue body was obtained.

5) The data was filtered using a 30-point moving average zero-phase filter.

6) The overall average value of the obtained intensity data was calculated, and the overall average value was used as the threshold. Then, it was determined whether the intensity data at one surface of the connective tissue body on the straight line L (that is, the intensity data at one end of the straight line L) is greater than or equal to the threshold. When the data was greater than or equal to the threshold, the determination was repeated from this end of the straight line L toward the other end, and the data portion that was greater than or equal to the threshold was identified as a "portion greater than or equal to the threshold." This "portion greater than or equal to the threshold" was identified as a "surface layer." Then, as the same determination was repeated toward the other end, the data became less than the threshold. The data portion that was less than the threshold was identified as a "portion less than the threshold", and this "portion less than the threshold" was identified as a "portion other than a surface layer."

When the intensity data at one surface of the connective tissue body on the straight line L (that is, the intensity data at one end of the straight line L) was less than the threshold, the determination was repeated from this end of the straight line L toward the other end, and the data portion that was less than the threshold was identified as a "portion less than the threshold." This "portion less than the threshold" was identified as a "surface layer." Then, as the same determination was repeated toward the other end, the data became greater than or equal to the threshold. The data portion that was greater than or equal to the threshold was identified as a "portion greater than or equal to the threshold", and this "portion greater than or equal to the threshold" was identified as a "portion other than a surface layer."

7) Then, on the straight line L, the average value (Y1) of the intensity data in the portion identified as the "surface layer" and the average value (Y2) of the intensity data in the portion identified as the "portion other than a surface layer" were calculated, and Y1/Y2 was defined as the tissue density ratio of the surface layer at one surface.

8) The tissue density ratio was calculated in the same manner for the surface layer at one surface of the connective tissue body for the remaining 29 images, and the average value of the tissue density ratios obtained from the 30 images was defined as the "tissue density ratio" of the surface layer at one surface.

If necessary, the tissue density ratio may be calculated in the same manner for the surface layer at the other surface.

Example 1

First, a connective tissue body formation substrate 10 including a cylindrical cover member 11 and a core member 12 as shown in FIG. 6 was prepared. The core member 12 had a center member 12B, which was formed by a stainless steel tube with an acrylic rod embedded therein, and a cover tube 12C made of silicone resin. The core member 12 had an outer diameter of 16 mm. The cover member 11 had an outer diameter of 19 mm and an inner diameter of 18 mm, had 1.5×15 mm slits, four in the axial direction and 11 in the circumferential direction, and was made of stainless steel. As such, the tissue formation surface formed by the core member 12 was made of silicone resin, and the tissue formation surface formed by the cover member 11 was made of stainless steel.

Then, an incision was made under anesthesia in the back skin of a beagle, which was 12 months old and weighed 8.5 kg, to form an insertion opening in the biological surface, and the subcutaneous tissue was dissected with scissors or the like through the insertion opening to create a subcutaneous pocket large enough to accommodate the connective tissue body formation substrate 10. Through the insertion opening, the connective tissue body formation substrate 10 was pushed in by hand to be implanted, and the insertion opening was sutured after the implantation. The needle of a syringe was then inserted through the skin to the substrate, and air was removed from the environment where the connective tissue body formation substrate 10 was implanted.

Then, after the beagle was kept for 60 days under a normal environment, an incision was made again to form an opening for removal in the biological surface. The connective tissue body formation substrate 10 on which a connective tissue body was formed was removed from the living body. Then, the connective tissue body was pulled out from the connective tissue body formation substrate 10 to obtain a cylindrical connective tissue body 30 as shown in FIG. 14. Before being pulled out from the connective tissue body formation substrate 10, the inner circumferential surface of the connective tissue body 30 was in contact with or faced the tissue formation surface (silicone resin) of the core member 12 of the connective tissue body formation substrate 10. Before being pulled out from the connective tissue body formation substrate 10, the outer circumferential surface of the connective tissue body 30 was in contact with or faced the tissue formation surface (stainless steel) of the cover member 11 of the connective tissue body formation substrate 10.

Figure 15:
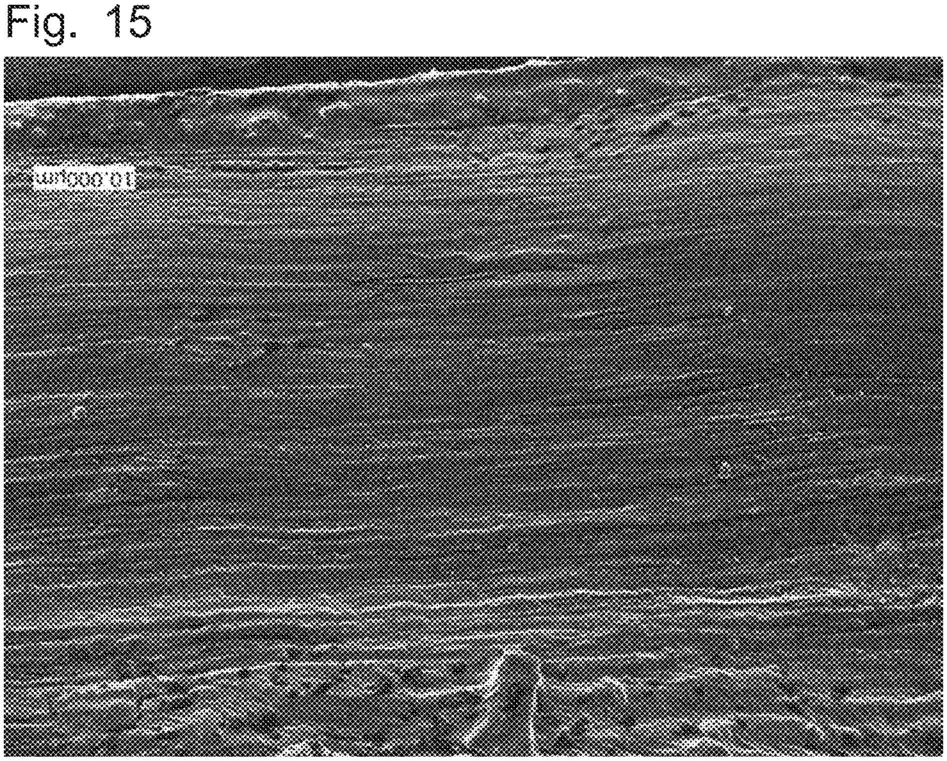
FIG. 15 is a photograph of a magnified cross-section of a connective tissue body of Example 1.
Figure 16:
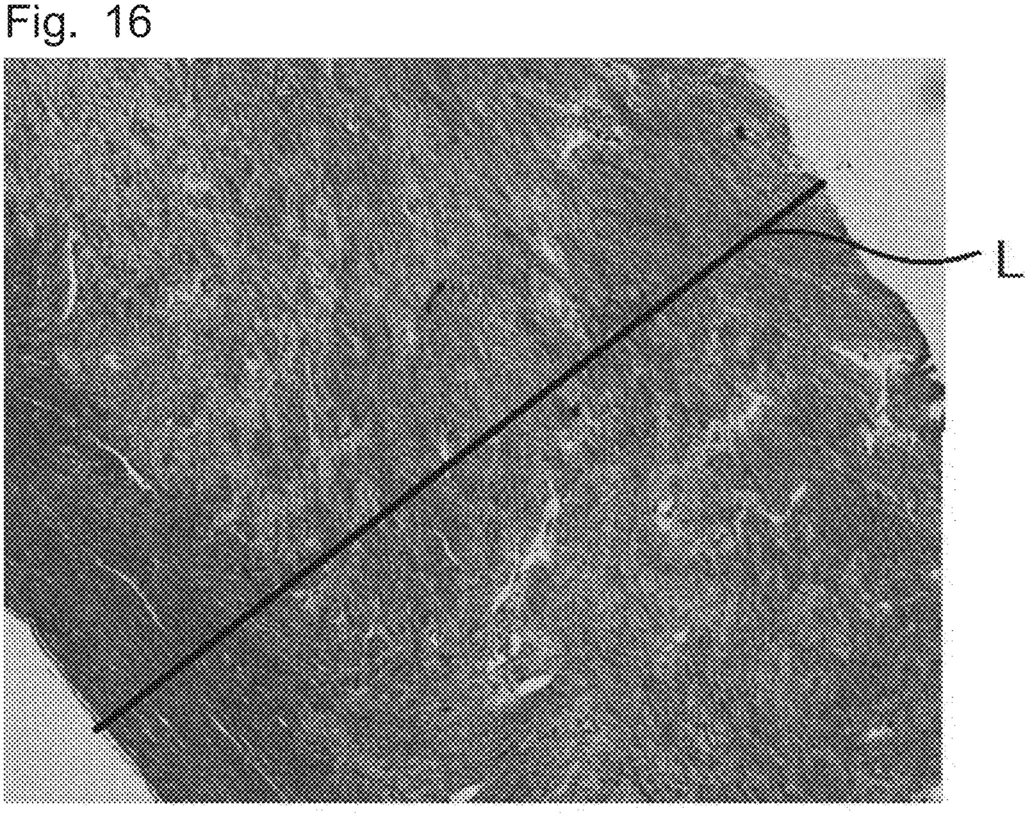
FIG. 16 is a photograph of a cross-section of a connective tissue body of Example 1 that is stained and captured under magnification.
Figure 17:
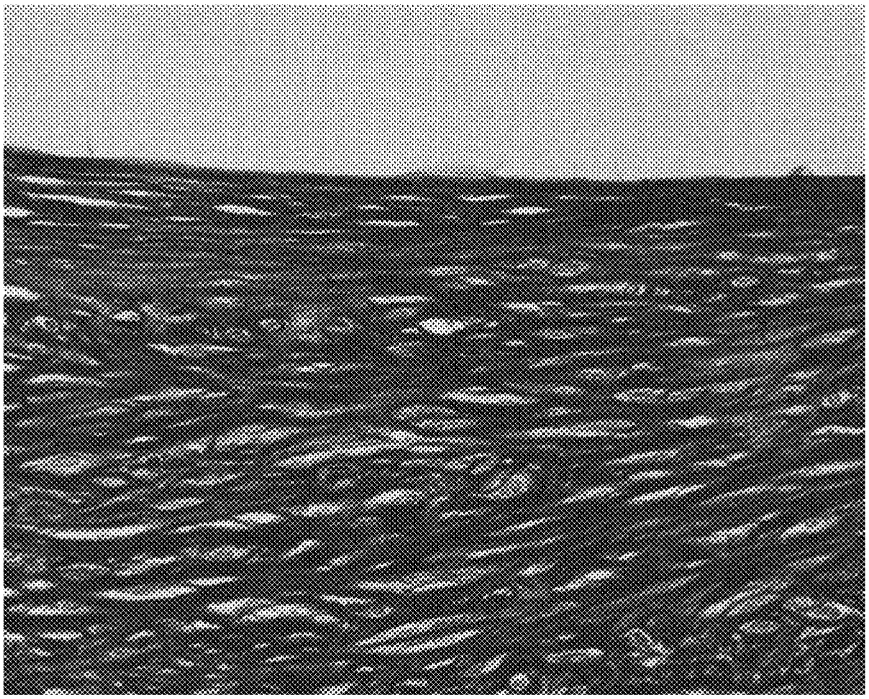
FIG. 17 is a photograph of a stained cross-section of the connective tissue body of Example 1, showing an enlarged view of a portion near the inner circumferential surface of the connective tissue body.
Figure 18:
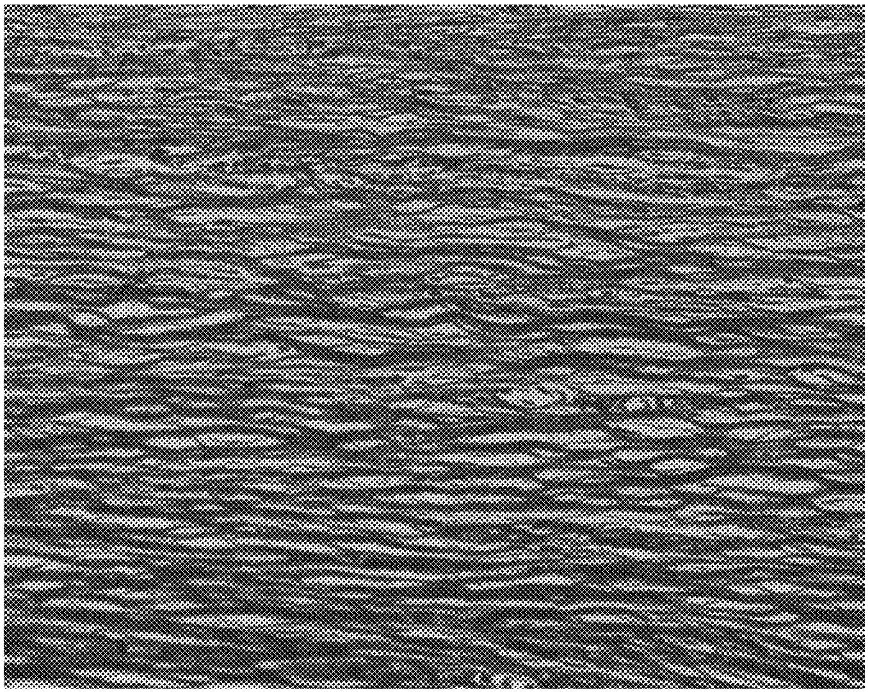
FIG. 18 is a photograph of a stained cross-section of the connective tissue body of Example 1, showing an enlarged view of a central portion in the thickness direction of the connective tissue body.

The obtained connective tissue body 30 was cut and observed with an electron microscope. FIG. 15 shows a photograph of the section. In FIG. 15, the upper side corresponds to the inner circumferential surface. Also, the obtained connective tissue body 30 was cut into sections in the manner described above, and the sections were stained with Masson's trichrome stain. FIGS. 16 to 18 show microscope photographs of the sections. FIG. 17 is an enlarged view of a portion near the inner circumferential surface of the connective tissue body 30. FIG. 18 is an enlarged view of a central portion in the thickness direction of the connective tissue body 30.

As shown in FIGS. 16 and 17, the portion at the inner circumferential surface of the cylindrical connective tissue body had dense connective tissue and few voids, indicating that a dense surface layer was formed.

In contrast, as shown in FIGS. 16 and 18, the portion other than the dense surface layer (for example, a central portion in the thickness direction) had many voids, indicating that the density inside the connective tissue body was lower than that of the surface layer.

The density of the surface layer at one surface (inner circumferential surface) was measured by the method described herein. As shown in the result in Table 1 below, the tissue density was 1.56. The tissue density of the surface layer at the other surface (outer circumferential surface) was 1.48.

TABLE 1

| Image No. | Intensity data: Surface layer | Intensity data: Non-surface layer | Tissue density ratio |
|---|---|---|---|
| 1 | 0.64 | 0.48 | 1.33 |
| 2 | 0.50 | 0.28 | 1.77 |
| 3 | 0.66 | 0.48 | 1.40 |
| 4 | 0.51 | 0.33 | 1.52 |
| 5 | 0.70 | 0.47 | 1.47 |
| 6 | 0.59 | 0.31 | 1.90 |
| 7 | 0.68 | 0.06 | 1.37 |

TABLE 1-continued

| Image No. | Intensity data: Surface layer | Intensity data: Non-surface layer | Tissue density ratio |
|---|---|---|---|
| 8 | 0.53 | 0.27 | 1.96 |
| 9 | 0.62 | 0.11 | 1.30 |
| 10 | 0.54 | 0.31 | 1.73 |
| 11 | 0.64 | 0.11 | 1.29 |
| 12 | 0.43 | 0.22 | 1.95 |
| 13 | 0.64 | 0.49 | 1.30 |
| 14 | 0.62 | 0.37 | 1.68 |
| 15 | 0.62 | 0.06 | 1.34 |
| 16 | 0.51 | 0.30 | 1.72 |
| 17 | 0.77 | 0.59 | 1.31 |
| 18 | 0.53 | 0.37 | 1.44 |
| 19 | 0.64 | 0.08 | 1.30 |
| 20 | 0.44 | 0.23 | 1.92 |
| 21 | 0.63 | 0.48 | 1.30 |
| 22 | 0.51 | 0.32 | 1.60 |
| 23 | 0.66 | 0.54 | 1.22 |
| 24 | 0.57 | 0.37 | 1.54 |
| 25 | 0.64 | 0.08 | 1.36 |
| 26 | 0.51 | 0.21 | 2.37 |
| 27 | 0.69 | 0.51 | 1.34 |
| 28 | 0.57 | 0.32 | 1.78 |
| 29 | 0.69 | 0.48 | 1.44 |
| 30 | 0.52 | 0.30 | 1.73 |
| Average | 0.59 | 0.32 | 1.56 |

Figure 19:
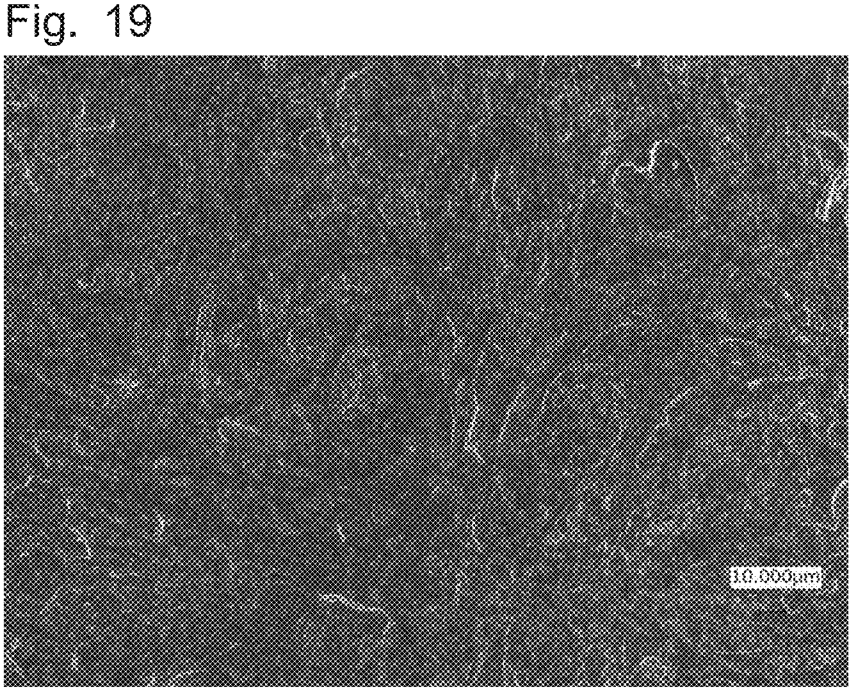
FIG. 19 is a photograph of the inner circumferential surface of the connective tissue body forming the surface of a dense surface layer of Example 1 captured under magnification.
Figure 20:
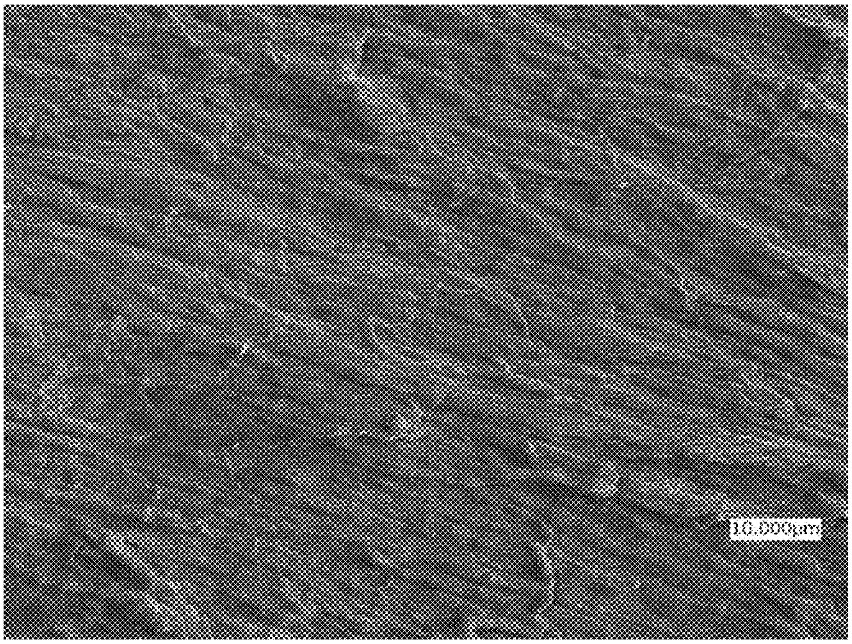
FIG. 20 is a photograph of the inside of the dense surface layer of the connective tissue body of Example 1 captured under magnification.
Figure 21:
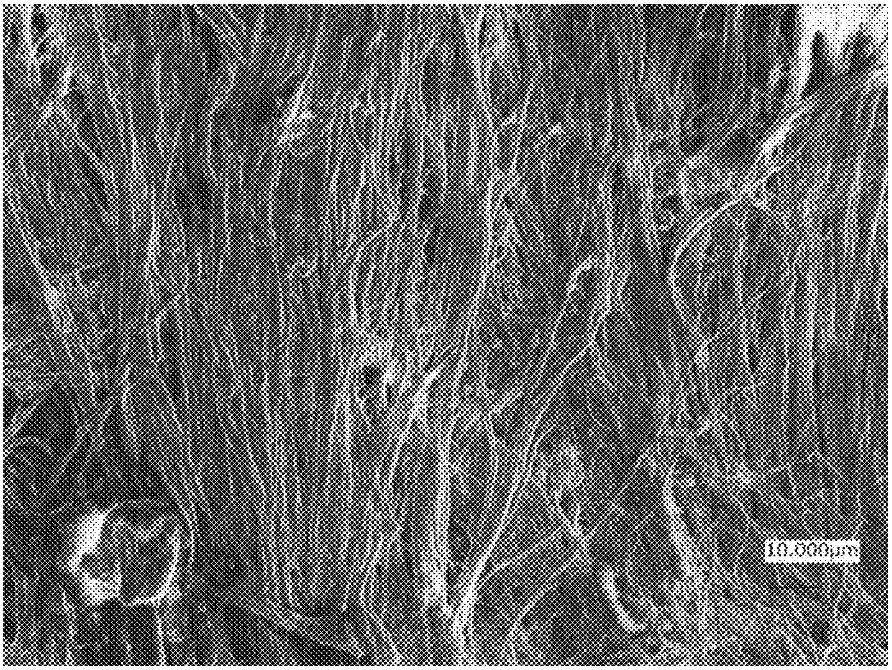
FIG. 21 is a photograph of a portion other than the dense surface layer of the connective tissue body of Example 1 captured under magnification.

FIG. 19 is an electron microscope photograph of the inner circumferential surface of the connective tissue body. FIG. 20 shows an electron microscope photograph of the condition of a surface of a dense surface layer other than the inner circumferential surface of the connective tissue body that was exposed by peeling off the inner circumferential surface. FIG. 21 is an electron microscope photograph of the condition of a portion other than the dense surface layer that was exposed by further peeling off the connective tissue body.

FIG. 19 shows that the surface of the dense surface layer was covered by flat, smooth collagen and that the collagen was randomly oriented rather than oriented in one direction. In contrast, as can be seen in FIG. 20, fibrous collagen was formed in bundles and oriented substantially in one direction in a portion of the dense surface layer other than the surface. Also, as is clear from the photographs of FIGS. 15 and 20, the fibrous collagen that was formed in bundles and oriented in one direction was formed in multiple layers. The photograph of FIG. 15 shows granular dots aligned in the lateral direction. This clearly indicates that the fibrous collagen in one layer of fibrous collagen bundles oriented in one direction was perpendicular to the fibrous collagen in another layer, so that the fibrous collagen was arranged in a mesh pattern. This mesh pattern was also formed on the inner side and observed in an inner portion of the connective tissue body with low density as shown in FIG. 21.

Also, as shown in FIG. 20, the collagen in the dense surface layer was dense and formed thick fibers. In contrast, as shown in FIG. 21, in a portion other than the dense surface layer, the fibrous collagen bundles were thinner than the collagen bundles in the dense surface layer.

Figure 23:
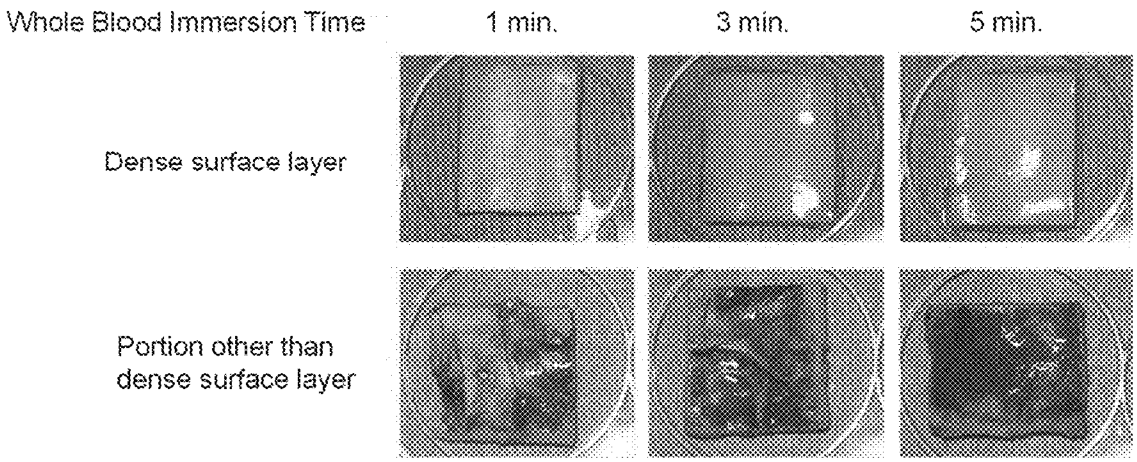
FIG. 23 shows connective tissue bodies after immersion in dog whole blood in Example 1.

The connective tissue body obtained in Example 1 was immersed in dog whole blood, removed after 1, 3, or 5 minutes, cleaned with physiological saline, and then photographed and observed. As shown in FIG. 23, all specimens were substantially free of blood coagulation, and no thrombus was formed.

Figure 24:
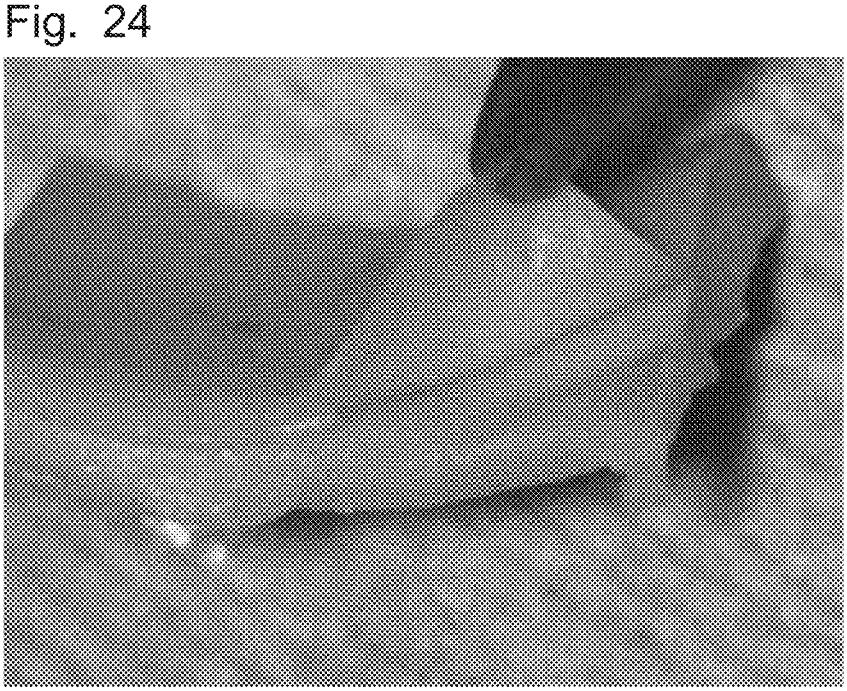
FIG. 24 is a photograph illustrating that Example 1 has a wall dissociation structure.

The dense surface layer of the connective tissue body obtained in Example 1 was peeled off to expose a portion other than the dense surface layer surface. The specimens thus obtained were immersed in dog whole blood and then removed after 1, 3, or 5 minutes. After cleaning with physiological saline, a photograph was taken and observed. As shown in FIG. 23, thrombi adhered to portions of the surface after 1 minute, and thrombus formation occurred on the entire surface after 5 minutes. As shown in FIG. 24, the dense surface layer was easily peeled off as a layer with tweezers and therefore had a wall dissociation structure.

The dense surface layer was peeled off, and the weight (B(g)) was measured. The layer was vacuum dried at 25° C. for 12 hours, and then the weight (A(g)) was measured. The moisture content ((B−A)/A×100) of the dense surface layer determined from the weight change was 56% on average. The average moisture content of a portion other than the dense surface layer obtained in the same manner was 73%. This indicates that the dense surface layer is less likely to absorb moisture than the other portions.

Example 2

A connective tissue body formation substrate 50 including a cylindrical cover member 51 and four core members 52 as shown in FIG. 10 was prepared. Each core member 52 was a stainless steel round bar sheathed with a silicone resin tube having an inner diameter of 1 mm and an outer diameter of 2 mm. The stainless steel round bar had an outer diameter of 1 mm. The cover member 51 had an outer diameter of 10 mm and an inner diameter of 8 mm. Round holes of 1.5 mm were evenly formed in a staggered pattern so as to have an aperture ratio of about 20% (the area ratio of the slits to the tissue formation surface of the cover member). The cover member 51 was made of stainless steel. The four core members 52 were arranged substantially evenly inside the cover member 51. As such, the tissue formation surface formed by each core member was made of silicone resin, and the tissue formation surface formed by the cover member was made of stainless steel.

Then, an incision was made under anesthesia in the abdominal skin of a domestic pig, which was 3 months old and weighed 40 kg, to form an insertion opening in the biological surface, and the subcutaneous tissue was dissected with scissors or the like through the insertion opening to create a subcutaneous pocket large enough to accommodate the connective tissue body formation substrate 50. Through the insertion opening, the connective tissue body formation substrate 50 was pushed in by hand to be implanted, and the insertion opening was sutured after the implantation. The needle of a syringe was then inserted through the skin to the substrate, and air was removed from the environment where the connective tissue body formation substrate 50 was implanted.

Then, after the pig was kept for 60 days under a normal environment, an incision was made again to form an opening for removal in the biological surface. The connective tissue body formation substrate 50 on which a connective tissue body was formed was removed from the living body. Then, the connective tissue body was pulled out from the connective tissue body formation substrate 50 to obtain a columnar connective tissue body 30 that had the cross-sectional structure shown in FIG. 3 and columnar hollow holes (hollow portions).

According to the method described herein, the densities of the surface layers around the hollow portions in the connective tissue body 30 (the inner circumferential surfaces) and the outer circumferential surface were measured. The density around the inner cavity was 1.4, and the density in the outer circumferential surface was 1.2.

Example 3

As shown in FIG. 12, a connective tissue body formation substrate 60 was prepared that included a stent as a dissimilar member 37 on the outer circumference of a columnar core member 62. The core member 62 was a round bar made of nylon resin and had an outer diameter of 15 mm. The stent was a balloon-expandable stent made of a cobalt chrome alloy and was expanded to an inner diameter of 16 mm. As such, the tissue formation surface formed by the core member 62 was nylon resin, and the tissue formation surface formed by the dissimilar member 37 was the cobalt chrome alloy.

Then, an incision was made under anesthesia in the back skin of a goat, which was 10 months old and weighed 35 kg, to form an insertion opening in the biological surface, and the subcutaneous tissue was dissected with scissors or the like through the insertion opening to create a subcutaneous pocket large enough to accommodate the connective tissue body formation substrate. Through the insertion opening, the connective tissue body formation substrate was pushed in by hand to be implanted, and the insertion opening was sutured after the implantation. The needle of a syringe was then inserted through the skin to the substrate, and air was removed from the environment where the connective tissue body formation substrate 60 was implanted.

After the goat was kept for 30 days under a normal environment, an incision was made again to form an opening for removal in the biological surface. The connective tissue body formation substrate on which a connective tissue body was formed was removed from the living body. Then, the connective tissue body was pulled out from the connective tissue body formation substrate to obtain a columnar connective tissue body 30 that had the cross-sectional structure shown in FIG. 4 and a columnar hollow hole (hollow portion).

According to the method described herein, the densities of the surface layer at one surface (inner circumferential surface) of the connective tissue body 30 and the surface layer around the inner stent were measured. The tissue density of the inner circumferential surface of the connective tissue body 30 was 1.2, while the tissue density of the surface layer around the stent was 1.1.

Example 4

A connective tissue body formation substrate 10 including a cylindrical cover member 11 and a core member 12 as shown in FIG. 11 was prepared, and a stent as a dissimilar member 37 was arranged in the gap between the cover member 11 and the core member 12. The core member 12 included a center member 12B made of PEEK resin and a cover tube 12C made of silicone resin. The core member 12 had an outer diameter of 20 mm. The cover member 11 had an outer diameter of 25 mm and an inner diameter of 23 mm, had 2 mm×20 mm slits, and was made of stainless steel. The stent was made of a nickel titanium alloy and had an inner diameter of 22 mm. As such, the tissue formation surface formed by the core member was PEEK resin, the tissue formation surface formed by the cover member was stainless steel, and the tissue formation surface formed by the stent was nickel titanium.

Then, an incision was made under anesthesia in the back skin of a goat, which was 12 months old and weighed 43 kg, to form an insertion opening in the biological surface, and the subcutaneous tissue was dissected with scissors or the like through the insertion opening to create a subcutaneous pocket large enough to accommodate the connective tissue body formation substrate 10. Through the insertion opening, the connective tissue body formation substrate 10 was pushed in by hand to be implanted, and the insertion opening was sutured after the implantation. The needle of a syringe was then inserted through the skin to the substrate, and air was removed from the environment where the connective tissue body formation substrate 10 was implanted.

Then, after the beagle was kept for 60 days under a normal environment, an incision was made again to form an opening for removal in the biological surface. The connective tissue body formation substrate 10 on which a connective tissue body was formed was removed from the living body. Then, the connective tissue body was pulled out from the connective tissue body formation substrate 10 to obtain a cylindrical connective tissue body 30 having the cross-sectional structure shown in FIG. 5.

According to the method described herein, the densities of the surface layer at one surface (inner circumferential surface) of the connective tissue body 30, the surface layer at the other surface (the outer circumferential surface), and the surface layer around the inner stent were measured. The tissue density of the inner circumferential surface of the connective tissue body 30 was 1.3, the tissue density of the outer circumferential surface of the connective tissue body 30 was 1.2, and the tissue density of the surface layer around the stent was 1.1.

Comparative Example 1

Figure 25:
FIG. 25 is a photograph of a cross-section of a connective tissue body of Comparative Example 1 that is stained and captured under magnification.
Figure 26:
FIG. 26 shows the connective tissue body of Comparative Example 1.
Figure 27:
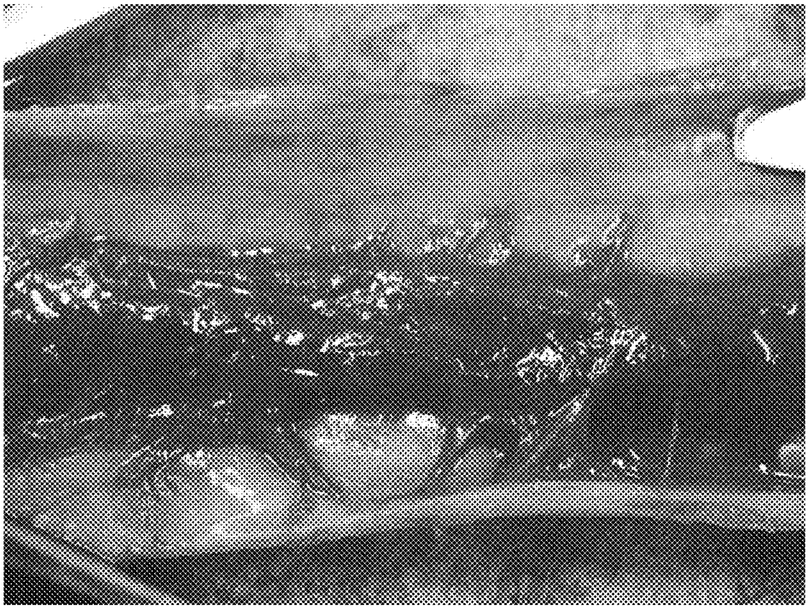
FIG. 27 shows the connective tissue body after immersion in dog whole blood in Comparative Example 1.

Comparative Example 1 was the same as Example 1 except that the step of removing air from the living body with a syringe was omitted. In Comparative Example 1, as shown in FIG. 25, blood clots were formed (in the upper portion on the left side), the connective tissue body was not sufficiently formed, and a dense surface layer was not formed. As shown in FIG. 26, liquid agglomerates were formed in red on portions of the white collagen surface layer. Also, the strength was insufficient, and there was a crack in the surface (the central portion in FIG. 26). The surface at the inner circumference of Comparative Example 1 was immersed in dog whole blood, removed after 1, 3, or 5 minutes, cleaned with physiological saline, and then photographed and observed. As shown in FIG. 27, thrombi were formed over the entire surface after 1 minute.

In the present disclosure, the removal of air (step 2) is effective at facilitating the contact between the tissue formation surfaces of the connective tissue body formation substrate 10 and living cells in the living body, or at improving the contact characteristics. The removal of air is also effective at promoting the encapsulation reaction on the connective tissue body formation substrate 10 in the living body, and at promoting the initiation of an encapsulation reaction, for example. The formation of the connective tissue body 30 by the encapsulation reaction begins on the tissue formation surface of the connective tissue body formation substrate 10 in the living body.

In the present disclosure, the formation speed (growth speed) of the connective tissue body 30 in the initial stage of the period in which the formation or growth of the connective tissue body 30 takes place (step 3) is one of the factors that affect the density (and the microscopic structure) of the surface layer including the surface of the connective tissue body 30 that is in contact with or faces the tissue formation surface of the connective tissue body formation substrate 10. The polymer material illustrated herein (or a combination of a polymer material and a metal material) is effective at lowering the formation speed (growth speed) of the connective tissue body in the initial stage of the period in which the formation or growth of the connective tissue body takes place (step 3) in an intended or controlled manner. The use of the polymer material illustrated herein (or a combination of a polymer material and a metal material) for the tissue formation surface of the connective tissue body formation substrate 10 is effective at allowing the connective tissue body 30 to have a dense surface layer whose density is adjusted to be relatively high. As the formation of a connective tissue body proceeds, the formation speed of the connective tissue body may become less affected by the material of the tissue formation surface. The selection of one or more materials of the tissue formation surface contributes to the formation of a connective tissue body in which the dense surface layer is relatively dense and the portion other than the dense surface layer is relatively sparse. The selection also helps to allow the dense surface layer and the portion other than the dense surface layer to have different microscopic structures. In some examples, the difference in density between the dense surface layer and the portion other than the dense surface layer, and the difference in microscopic structure, which may be gradual variations, between the dense surface layer and the portion other than the dense surface layer can be observed as a wall dissociation structure described above as a functional characteristic, and also visually perceived under a microscope as a clear or blurred boundary between layers.

The portion of the connective tissue body 30 other than the surface layer, which is less dense than the dense surface layer, may be referred to as a non-surface-layer portion, a main body portion, or a base portion of the connective tissue body. The collagen forming the dense surface layer of the connective tissue body 30 may be referred to as first fibrous collagen, and the collagen forming the non-surface-layer portion of the connective tissue body 30 may be referred to as second fibrous collagen. The structure and density of the first fibrous collagen in the dense surface layer of the connective tissue body 30 may be referred to as a first microscopic structure and a first density, respectively. The structure and density of the second fibrous collagen in the non-surface-layer portion of the connective tissue body 30 may be referred to as a second microscopic structure and a second density, respectively. The structure and density of the first fibrous collagen impart a first blood permeation resistance to the dense surface layer, and the structure and density of the second fibrous collagen impart a second blood permeation resistance to the non-surface-layer portion. The first blood permeation resistance of the dense surface layer is higher than the second blood permeation resistance of the non-surface-layer portion. The wall dissociation structure of the present disclosure may also be referred to as a biological peelable boundary formed by the first fibrous collagen of the surface layer and the second fibrous collagen of the non-surface-layer portion. The connective tissue body 30 of the present disclosure may be referred to as an implantable product including biological origin collagen. The connective tissue body 30 of the present disclosure may be an artificial organ for regenerative medicine or a part thereof.

DESCRIPTION OF THE REFERENCE NUMERALS

10 . . . Connective Tissue Body Formation Substrate
11 . . . Cover Member

12 . . . Core Member
11A, 12A . . . Tissue Formation Surface
13 . . . Tissue Formation Space
14, 15 . . . Lid
17 . . . Hole
18 . . . Insertion Opening
19 . . . Guide Rod
20 . . . Insertion Tube
21 . . . Push Rod
22 . . . Space
30 . . . Connective Tissue Body
30A . . . Outer Circumferential Surface
30B . . . Inner Circumferential Surface
31 . . . Ridges
32 . . . Dense Surface Layer
35 . . . Hollow Portion
37 . . . Dissimilar Member
40 . . . Connective Tissue Body Formation Substrate
41 . . . Cover Member
41A . . . Upper Member
41B . . . Lower Member
42 . . . Core Member
42E . . . Ends
43A . . . Coupling Member
43B . . . Coupling Member
47 . . . Holes
50 . . . Connective Tissue Body Formation Substrate
51 . . . Cover Member
52 . . . Core Members
54 . . . Lid
54A . . . Locking Portion
55 . . . Lid
55A . . . Locking Portion
60 . . . Connective Tissue Body Formation Substrate
62 . . . Core Member

The invention claimed is:

1. A method for producing a connective tissue body including a surface layer, a non-surface-layer portion, which is other than the surface layer, and biological origin tissue including collagen, the method comprising:

placing, in a living body, a connective tissue body formation substrate including a tissue formation surface that is at least partially made of a polymer material, wherein the step of placing the connective tissue body formation substrate in the living body forms an internal space that accommodates the connective tissue body formation substrate in the living body;

removing air percutaneously and transluminally from the internal space that accommodates the connective tissue body formation substrate to an outside of the living body by applying a negative pressure to the internal space, wherein the step of removing air is configured to facilitate contact between the tissue formation surface of the connective tissue body formation substrate and living cells in the living body, thereby promoting production of collagen by the living cells contacting the tissue formation surface of the connective tissue body formation substrate and formation of the connective tissue body, which includes the biological origin tissue containing the collagen produced by the living cells, on the tissue formation surface of the connective tissue body formation substrate in the internal space of the living body;

leaving the connective tissue body formation substrate in the internal space of the living body to allow the connective tissue body, including the surface layer, the non-surface-layer portion, and the biological origin tissue containing the collagen produced by the living cells, to form on the tissue formation surface wherein, in the step of leaving the connective tissue body formation substrate in the internal space of the living body, the surface laver is in contact with the tissue formation surface of the connective tissue body formation substrate, the non-surface-layer portion is not in contact with the tissue formation surface of the connective tissue body formation substrate, and the collagen, including fibrous collagen, forms a continuous structure of the Collagen throughout a thickness direction of the connective tissue body including the surface layer and the non-surface-layer portion;

removing, from the living body, the connective tissue body formation substrate on which the connective tissue body is formed; and peeling off the connective tissue body from the connective tissue body formation substrate to obtain the connective tissue body that includes the surface layer and the non-surface-layer portion, wherein the surface layer of the connective tissue body is a dense surface layer in which the biological origin tissue is denser than in the non-surface-layer portion, and wherein, for the dense surface layer, a ratio of a tissue density of the surface layer to a tissue density of the non-surface-layer portion that is calculated along the thickness direction is greater than or equal to 1.1, which allows the surface layer to be peelable off from the non-surface-layer portion.

2. The method according to claim 1, wherein:

the surface layer and the non-surface-layer portion form a biological peelable boundary therebetween where the surface layer is peelable off from the non-surface-layer portion.

3. The method according to claim 1, wherein the step of removing air is configured to facilitate contact between the tissue formation surface of the connective tissue body formation substrate and the living cells in the living body by drawing some of the living cells into the substrate.

4. A connective tissue body used for tissue transplantation, the connective tissue body comprising a surface layer, a non-surface-layer portion, which is other than the surface layer, and biological origin tissue including collagen produced by living cells in a living body, wherein, the surface layer of the connective tissue body is a dense surface layer in which the biological origin tissue is denser than in the non-surface-layer portion, the collagen, including fibrous collagen, forms a continuous structure of the collagen throughout a thickness direction of the connective tissue body including the surface layer and the non-surface-layer portion, and for the dense surface layer, a ratio of a tissue density of the surface layer to a tissue density of the non-surface-layer portion that is calculated along the thickness direction is greater than or equal to 1.1, which allows the surface layer to be peelable off from the non-surface-layer portion.

5. The connective tissue body according to claim 4, wherein the surface layer and the non-surface-layer portion form a biological peelable boundary therebetween where the surface layer is peelable off from the non-surface-layer portion.

6. A method for producing a connective tissue body that includes a surface layer, a non-surface-layer portion, which is other than the surface layer, and biological origin tissue including collagen and is used for tissue transplantation, the method comprising:

placing, in a living body other than a human body, a connective tissue body formation substrate including a tissue formation surface that is at least partially made of a polymer material, wherein the step of placing the connective tissue body formation substrate in the living body forms an internal space that accommodates the connective tissue body formation substrate in the living body;

removing air percutaneously and transluminally from the internal space that accommodates the connective tissue body formation substrate to an outside of the living body by applying a negative pressure to the internal space, wherein the step of removing air is configured to facilitate contact between the tissue formation surface of the connective tissue body formation substrate and living cells in the living body, thereby promoting production of collagen by the living cells contacting the tissue formation surface of the connective tissue body formation substrate and formation of the connective tissue body, which includes the biological origin tissue containing the collagen produced by the living cells, on the tissue formation surface of the connective tissue body formation substrate in the internal space of the living body;

leaving the connective tissue body formation substrate in the internal space of the living body to allow the connective tissue body, including the surface layer, the non-surface-layer portion, and the biological origin tissue containing the collagen produced by the living cells, to form on the tissue formation surface wherein, in the step of leaving the connective tissue body formation substrate in the internal space of the living body, the surface laver is in contact with the tissue formation surface of the connective tissue body formation substrate, the non-surface-layer portion is not in contact with the tissue formation surface of the connective tissue body formation substrate, and the collagen, including, fibrous collagen forms a continuous structure of the collagen throughout a thickness direction of the connective tissue body including the surface layer and the non-surface-layer portion;

removing, from the living body, the connective tissue body formation substrate on which the connective tissue body is formed; and peeling off the connective tissue body from the connective tissue body formation substrate to obtain the connective tissue body that includes the surface layer and the non-surface-layer portion, wherein the surface layer of the connective tissue body is a dense surface layer in which the biological origin tissue is denser than in the non-surface-layer portion, and wherein, for the dense surface layer, a ratio of a tissue density of the surface layer to a tissue density of the non-surface-layer portion that is calculated along the thickness direction is greater than or equal to 1.1, which allows the surface laver to be peelable off from the won-surface-layer portion.

7. The method for producing a connective tissue body according to claim 6, wherein the connective tissue body is formed by an encapsulation reaction.

8. The method according to claim 6, wherein:

the surface layer and the non-surface-layer portion form a biological peelable boundary therebetween where the surface layer is peelable off from the non-surface-layer portion.

9. The method according to claim 6, wherein the step of removing air is configured to facilitate contact between the tissue formation surface of the connective tissue body formation substrate and the living cells in the living body by drawing some of the living cells into the substrate.

* * * * *